(12) United States Patent
Chopra et al.

(10) Patent No.: US 9,085,546 B2
(45) Date of Patent: *Jul. 21, 2015

(54) AMIDE GELLANT COMPOSITIONS CONTAINING ISOSORBIDE

(75) Inventors: Naveen Chopra, Oakville (CA); Michelle N. Chrétien, Mississauga (CA); Barkev Keoshkerian, Thornhill (CA); Daryl Vanbesien, Burlington (CA); Jenny Eliyahu, Maple (CA)

(73) Assignee: XEROX CORPORATION, Norwalk, CT (US)

( * ) Notice: Subject to any disclaimer, the term of this patent is extended or adjusted under 35 U.S.C. 154(b) by 305 days.

This patent is subject to a terminal disclaimer.

(21) Appl. No.: 13/442,559

(22) Filed: Apr. 9, 2012

(65) Prior Publication Data

US 2013/0267718 A1 Oct. 10, 2013

(51) Int. Cl.
*A61K 31/075* (2006.01)
*A61K 31/16* (2006.01)
*A61K 31/335* (2006.01)
*A61K 31/34* (2006.01)
*C07D 319/12* (2006.01)
*C07D 493/04* (2006.01)
*C07D 519/00* (2006.01)
*C09D 11/101* (2014.01)
*C09D 11/34* (2014.01)

(52) U.S. Cl.
CPC ............ *C07D 319/12* (2013.01); *A61K 31/075* (2013.01); *A61K 31/16* (2013.01); *A61K 31/335* (2013.01); *A61K 31/34* (2013.01); *C07D 493/04* (2013.01); *C07D 519/00* (2013.01); *C09D 11/101* (2013.01); *C09D 11/34* (2013.01)

(58) Field of Classification Search
CPC ... A61K 31/075; A61K 31/16; A61K 31/335; A61K 31/34
USPC ........................................ 549/464
See application file for complete search history.

(56) References Cited

U.S. PATENT DOCUMENTS

| | | | |
|---|---|---|---|
| 4,490,731 A | 12/1984 | Vaught | |
| 5,195,430 A | 3/1993 | Rise | |
| 5,231,135 A | 7/1993 | Machell | |
| 5,621,022 A | 4/1997 | Jaeger | |
| 5,783,657 A | 7/1998 | Pavlin | |
| 6,111,055 A | 8/2000 | Berger | |
| 6,221,137 B1 | 4/2001 | King | |
| 6,472,523 B1 | 10/2002 | Banning | |
| 6,476,219 B1 | 11/2002 | Duff | |
| 6,576,747 B1 | 6/2003 | Carlini | |
| 6,576,748 B1 | 6/2003 | Carlini | |
| 6,590,082 B1 | 7/2003 | Banning | |
| 6,646,111 B1 | 11/2003 | Carlini | |
| 6,663,703 B1 | 12/2003 | Wu | |
| 6,673,139 B1 | 1/2004 | Wu | |
| 6,696,552 B2 | 2/2004 | Mayo | |
| 6,713,614 B2 | 3/2004 | Carlini | |
| 6,726,755 B2 | 4/2004 | Titterington | |
| 6,755,902 B2 | 6/2004 | Banning et al. | |
| 6,821,327 B2 | 11/2004 | Jaeger | |
| 6,958,406 B2 | 10/2005 | Banning | |
| 7,053,227 B2 | 5/2006 | Jaeger | |
| 7,186,762 B2 | 3/2007 | Wong | |
| 7,276,614 B2 | 10/2007 | Toma | |
| 7,279,584 B2 | 10/2007 | Tomisawa | |
| 7,279,587 B2 | 10/2007 | Odell | |
| 7,296,614 B2 | 11/2007 | Schlichting | |
| 7,381,831 B1 | 6/2008 | Banning | |
| 7,427,323 B1 | 9/2008 | Birau | |
| 7,559,639 B2 | 7/2009 | Belelie | |
| 2006/0122415 A1 | 6/2006 | Carlini et al. | |
| 2007/0120910 A1 | 5/2007 | Odell | |
| 2008/0122914 A1 | 5/2008 | Toma | |
| 2008/0218540 A1 | 9/2008 | Iftime | |
| 2011/0152397 A1 | 6/2011 | Breton | |
| 2011/0196057 A1 | 8/2011 | Breton | |
| 2011/0196058 A1 | 8/2011 | Breton | |
| 2011/0263890 A1 | 10/2011 | Chopra et al. | |

OTHER PUBLICATIONS

Noordover et al. ("Enhancing the Functionality of Biobased Polyester Coating Resins through Modification with Citric Acid" Biomacromolecules, 2007, 8, 3860-3870).*
Thiem et al. "Condensation Reactions" Polymer Bulletin 11, 1984, 365-369.*
U.S. Appl. No. 12/765,148, filed Apr. 22, 2010, Chopra.
U.S. Appl. No. 12/972,138, filed Dec. 17, 2010, Breton.

* cited by examiner

*Primary Examiner* — Yong Chong
(74) *Attorney, Agent, or Firm* — Pillsbury Winthrop Shaw Pittman LLP

(57) ABSTRACT

Disclosed herein are ester-terminated polyamide gellant compounds end-caped with isosorbide and UV curable ink compositions containing them.

12 Claims, 6 Drawing Sheets

AMIDE GELLANT COMPOSITIONS CONTAINING ISOSORBIDE

BACKGROUND OF THE DISCLOSURE

The present disclosure relates to ink compositions, which are solid at room temperature and liquid at elevated temperatures. These solid ink compositions comprise an amide gellant with terminal groups.

Ink jet printing processes generally may employ inks that are solid at room temperature and liquid at elevated temperatures. Such inks may be referred to as solid inks, hot melt inks, phase change inks and the like. For example, U.S. Pat. No. 4,490,731, the disclosure of which is totally incorporated herein by reference, discloses an apparatus for dispensing solid ink for printing on a recording medium such as paper. In thermal ink jet printing processes employing hot melt inks, the solid ink is melted by the heater in the printing apparatus and utilized (jetted) as a liquid in a manner similar to that of conventional thermal ink jet printing. Upon contact with the printing recording medium, the molten ink solidifies rapidly, allowing the colorant to substantially remain on the surface of the recording medium instead of being carried into the recording medium (for example, paper) by capillary action, thereby enabling higher print density than is generally obtained with liquid inks. Advantages of solid inks in ink jet printing are thus elimination of potential spillage of the ink during handling, a wide range of print density and quality, minimal paper cockle or distortion, reduced print-through and enablement of indefinite periods of nonprinting without the danger of nozzle clogging, even without capping the nozzles.

Solid inks are desirable for ink jet printers because they remain in a solid phase at room temperature during shipping, long term storage, and the like. In addition, the problems associated with liquid ink jet inks such as nozzle clogging as a result of ink evaporation are largely eliminated, thereby improving the reliability of the ink jet printing. Further, in solid ink jet printers, wherein the ink droplets are applied directly onto the final recording medium (for example, paper, transparency material, and the like), the droplets solidify immediately upon contact with the recording medium, so that migration of ink along the printing medium is prevented and dot quality is improved.

Curable solid inks were conceived as a means to use conventional solid ink print process, especially transfix, and deliver an increase in mechanical robustness after curing. One of the challenges in formulating a suitable curable solid ink is to create a solid ink with sufficient molecular mobility to allow rapid and extensive curing. Previous formulations have been disclosed in U.S. Publication No. 2011/0196057 to Breton et al., which proposes use of an IGEPAL waxy derivative to increase cure speed. Reference is also made to U.S. Publication No. 2011/0152397 to Breton et al., U.S. Publication No. 2011/0196058 to Breton et al., and U.S. application Ser. No. 12/972,138 to Breton et al., the disclosures of which are incorporated herein by reference in their entireties.

Curable inks generally contain a gellant, such as a curable ester-terminated amide gellant that may be end-capped with a suitable molecule. Typical ester 'end-caps' on gellant molecules include specialty materials such as photoinitiators, acrylates, and aromatic alcohols such as benzyl alcohol and phenylethyl alcohol. U.S. Pat. No. 7,296,614 (Toma et al) discloses and claims curable amide gellants wherein the end caps have at least 1 ethylenically unsaturation. U.S. Pat. No. 7,279,584 (Odell et al) discloses and claims photoinitiators with phase change properties and gellant affinity, wherein the end caps have at least 1 photoinitiating group. U.S. Pat. No. 5,783,657 (Pavlin et al) and U.S. Pat. No. 6,111,055 (Berger et al) disclose and claim ester terminated polyamides for gelling of hydrocarbon solvents (i.e. candles), wherein the end caps have alkyl and alkenyl groups of at least 4 C atoms, such as C12-C22. While the above conventional solid ink technology is generally successful in producing suitable solid inks, there is still a need for an improved curable solid inks that are sourced from materials with increased bio-renewable content (BRC).

Each of the foregoing U.S. patents and patent Publications are incorporated by reference herein. Further, the appropriate components and process aspects of each of the foregoing U.S. patents and patent Publications may be selected for the present disclosure in embodiments thereof.

SUMMARY OF THE DISCLOSURE

Disclosed herein are curable ester-terminated polyamide compounds that are end-capped with isosorbide and ink compositions containing them.

According to some embodiments, amide gellant compounds are provided having the formula:

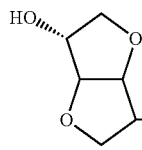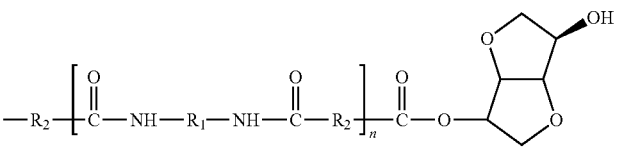

wherein n is 0 to 10, and wherein $R_1$ is selected from the group consisting of: (i) a substituted or unsubstituted alkylene group having from about 1 carbon atom to about 12 carbon atoms, (ii) a substituted or unsubstituted arylene group having from about 1 carbon atom to about 15 carbon atoms, (iii) a substituted or unsubstituted arylalkylene group having from about 6 carbon atoms to about 32 carbon atoms, and (iv) a substituted or unsubstituted alkylarylene group having from about 5 carbon atoms to about 32 carbon atoms; and wherein $R_2$ is selected from the group consisting of: (i) substituted or unsubstituted alkylene groups having from about 1 carbon atom to about 54 carbon atoms, (ii) substituted or unsubstituted arylene groups having from about 5 carbon atoms to about 15 carbon atoms, (iii) substituted or unsubstituted arylalkylene groups having from about 6 carbon atoms to about 32 carbon atoms, and (iv) substituted or unsubstituted alkylarylene groups having from about 6 carbon atoms to about 32 carbon atoms.

In some embodiments, the alkylene group of $R_1$ or $R_2$ is a divalent aliphatic group or alkyl group, including linear and branched, saturated and unsaturated, and cyclic and acyclic. The alkylene group may optionally comprise heteroatoms selected from the group consisting of oxygen, nitrogen, sulfur, silicon, phosphorus, and boron.

In some embodiments, the arylene group of $R_1$ or $R_2$ is a divalent aromatic group or aryl group. The alkylene group may optionally comprise heteroatoms selected from the group consisting of oxygen, nitrogen, sulfur, silicon, phosphorus, and boron.

In some embodiments, the arylalkylene group of $R_1$ or $R_2$ is a divalent arylalkyl group. The alkyl portion of the arylalkylene group may be linear or branched, saturated or unsaturated, and cyclic or acyclic. The alkylene group, in either the aryl or the alkyl portion of the arylalkylene group, may optionally comprise heteroatoms selected from the group consisting of oxygen, nitrogen, sulfur, silicon, phosphorus, and boron.

In some embodiments, the alkylarylene group of $R_1$ or $R_2$ is a divalent alkylaryl group. The alkyl portion of the alkylarylene group may be linear or branched, saturated or unsaturated, and cyclic or acyclic. The alkylarylene group, in either the aryl or the alkyl portion of the alkylarylene group, may optionally comprise heteroatoms selected from the group consisting of oxygen, nitrogen, sulfur, silicon, phosphorus, and boron.

In some embodiments, the substituents on substituted alkylene, arylene, arylalkylene, and alkylarylene groups of $R_1$ or $R_2$ may be selected from the group consisting of halogen atoms, cyano groups, pyridine groups, pyridinium groups, ether groups, aldehyde groups, ketone groups, ester groups, amide groups, carbonyl groups, thiocarbonyl groups, phosphine groups, phosphonium groups, phosphate groups, nitrile groups, mercaptosulfide groups, nitro groups, nitroso groups, acyl groups, acid anhydride groups, azide groups, azo groups, cyanato groups, urethane groups, and urea groups.

In some embodiments, $R_2$ of the amide gellant compound of the above formula may be:

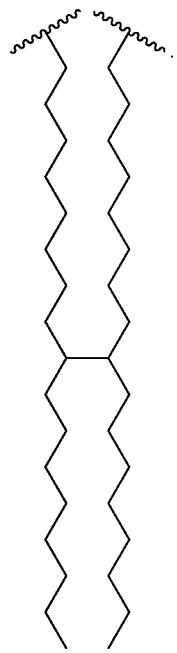 [SMILES: *CCCCCCCCC(CCCCCCCC)C(CCCCCCCC)CCCCCCCC*]

According to some embodiments, an amide gellant compound is provided having the formula:

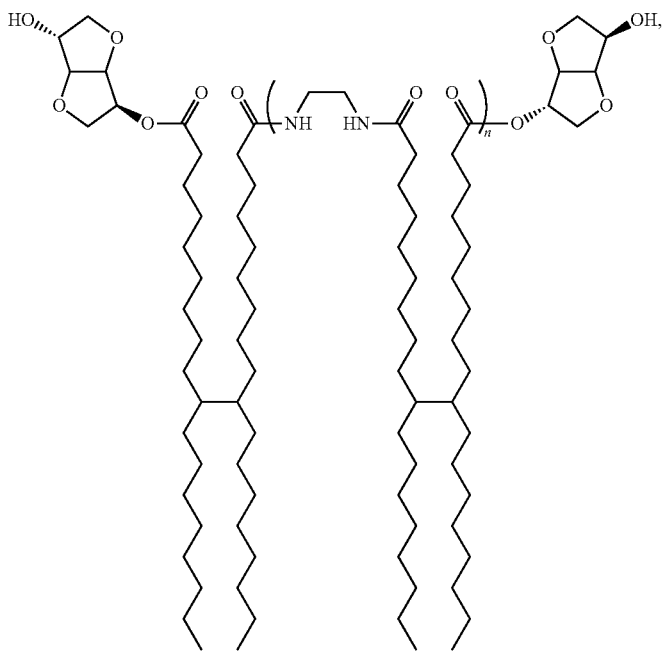

where n is 0 to 10.

DETAILED DESCRIPTION

Figure 1:
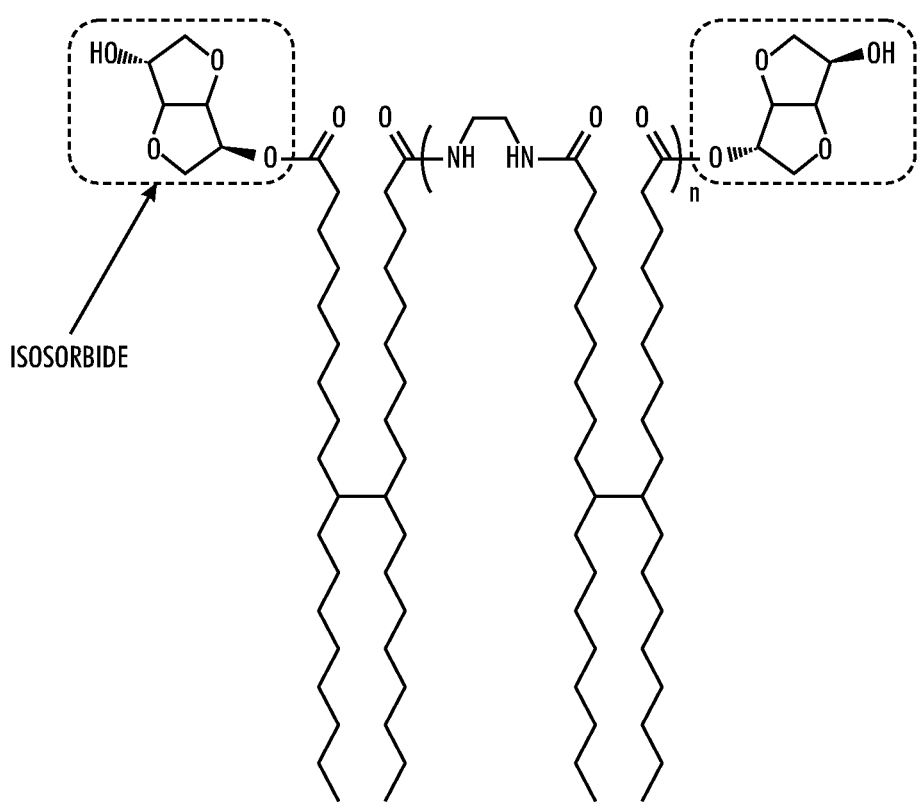
FIG. 1. Isosorbide End Capped Amide Gellant.

Disclosed herein are phase-change gelling agents enabling wide substrate latitude, excellent adhesion, and enhanced pigment dispersion stability. In some embodiments, the phase change gelling agent ('gellant') is an ester-terminated polyamide resin. The ester 'end caps' of the present embodiments are sourced from materials with increased bio-renewable content (BRC).

In some embodiments, the amide gellants are curable ester-terminated polyamide compounds that are end-capped with isosorbide. Amide gellants suitable for use include those described in U.S. Patent Application Publication No. 2008/0122914 and U.S. Pat. Nos. 7,276,614 and 7,279,587, the entire disclosures of which are incorporated herein by reference. Additional gellants suitable for use also include those described in U.S. patent application Ser. No. 12/765,148 to Chopra et al. filed on Apr. 22, 2010, the entire disclosure of which is incorporated herein by reference.

The amide gellants suitable for use in the composition may be amphiphilic in nature in order to improve wetting when the composition is utilized over a substrate having silicone or other oil thereon. Amphiphilic refers to molecules that have both polar and non-polar parts of the molecule. For example, the gellants may have long non-polar hydrocarbon chains and polar amide linkages.

In some embodiments, the amide gellant is a compound of the formula:

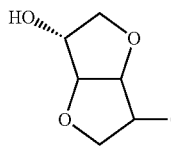 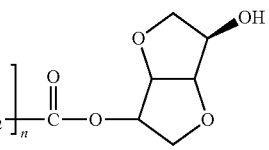

wherein n is 0 to 20 (i.e., 1, 2, 3, 4, 5, 6, 7, 8, 9, 10, 11, 12, 13, 14, 15, 16, 17, 18, 19, or 20) or n is 0 to 10, and wherein:

$R_1$ is:

(i) an alkylene group (wherein an alkylene group is a divalent aliphatic group or alkyl group, including linear and branched, saturated and unsaturated, cyclic and acyclic, and substituted and unsubstituted alkylene groups, and wherein heteroatoms, such as oxygen, nitrogen, sulfur, silicon, phosphorus, boron, and the like either may or may not be present in the alkylene group) having from about 1 carbon atom to about 12 carbon atoms, such as from about 1 carbon atom to about 8 carbon atoms or from about 1 carbon atom to about 5 carbon atoms, (ii) an arylene group (wherein an arylene group is a divalent aromatic group or aryl group, including substituted and unsubstituted arylene groups, and wherein heteroatoms, such as oxygen, nitrogen, sulfur, silicon, phosphorus, boron, and the like either may or may not be present in the arylene group) having from about 1 carbon atom to about 15 carbon atoms, such as from about 3 carbon atoms to about 10 carbon atoms or from about 5 carbon atoms to about 8 carbon atoms, (iii) an arylalkylene group (wherein an arylalkylene group is a divalent arylalkyl group, including substituted and unsubstituted arylalkylene groups, wherein the alkyl portion of the arylalkylene group can be linear or branched, saturated or unsaturated, and cyclic or acyclic, and wherein heteroatoms, such as oxygen, nitrogen, sulfur, silicon, phosphorus, boron, and the like either may or may not be present in either the aryl or the alkyl portion of the arylalkylene group) having from about 6 carbon atoms to about 32 carbon atoms, such as from about 6 carbon atoms to about 22 carbon atoms or from about 6 carbon atoms to about 12 carbon atoms, or (iv) an alkylarylene group (wherein an alkylarylene group is a divalent alkylaryl group, including substituted and unsubstituted alkylarylene groups, wherein the alkyl portion of the alkylarylene group can be linear or branched, saturated or unsaturated, and cyclic or acyclic, and wherein heteroatoms, such as oxygen, nitrogen, sulfur, silicon, phosphorus, boron, and the like either may or may not be present in either the aryl or the alkyl portion of the alkylarylene group) having from about 5 carbon atoms to about 32 carbon atoms, such as from about 6 carbon atoms to about 22 carbon atoms or from about 7 carbon atoms to about 15 carbon atoms, wherein the substituents on the substituted alkylene, arylene, arylalkylene, and alkylarylene groups can be halogen atoms, cyano groups, pyridine groups, pyridinium groups, ether groups, aldehyde groups, ketone groups, ester groups, amide groups, carbonyl groups, thiocarbonyl groups, sulfide groups, nitro groups, nitroso groups, acyl groups, azo groups, urethane groups, urea groups, mixtures thereof, and the like, wherein two or more substituents can be joined together to form a ring;

$R_2$ is:

(i) an alkylene group (wherein an alkylene group is a divalent aliphatic group or alkyl group, including linear and branched, saturated and unsaturated, cyclic and acyclic, and substituted and unsubstituted alkylene groups, and wherein heteroatoms, such as oxygen, nitrogen, sulfur, silicon, phosphorus, boron, and the like either may or may not be present in the alkylene group) having from about 1 carbon atom to about 54 carbon atoms, such as from about 1 carbon atom to about 48 carbon atoms or from about 1 carbon atom to about 36 carbon atoms, (ii) an arylene group (wherein an arylene group is a divalent aromatic group or aryl group, including substituted and unsubstituted arylene groups, and wherein heteroatoms, such as oxygen, nitrogen, sulfur, silicon, phosphorus, boron, and the like either may or may not be present in the arylene group) having from about 5 carbon atoms to about 15 carbon atoms, such as from about 5 carbon atoms to about 13 carbon atoms or from about 5 carbon atoms to about 10 carbon atoms, (iii) an arylalkylene group (wherein an arylalkylene group is a divalent arylalkyl group, including substituted and unsubstituted arylalkylene groups, wherein the alkyl portion of the arylalkylene group can be linear or branched, saturated or unsaturated, and cyclic or acyclic, and wherein heteroatoms, such as oxygen, nitrogen, sulfur, silicon, phosphorus, boron, and the like either may or may not be present in either the aryl or the alkyl portion of the arylalkylene group) having from about 6 carbon atoms to about 32 carbon atoms, such as from about 7 carbon atoms to about 33 carbon atoms or from about 8 carbon atoms to about 15 carbon atoms, or (iv) an alkylarylene group (wherein an alkylarylene group is a divalent alkylaryl group, including substituted and unsubstituted alkylarylene groups, wherein the alkyl portion of the alkylarylene group can be linear or branched, saturated or unsaturated, and cyclic or acyclic, and wherein heteroatoms, such as oxygen, nitrogen, sulfur, silicon, phosphorus, boron, and the like either may or may not be present in either the aryl or the alkyl portion of the alkylarylene group) having from about 6 carbon atoms to about 32 carbon atoms, such as from about 6 carbon atoms to about 22 carbon atoms or from about 7 carbon atoms to about 15 carbon atoms, wherein the substituents on any substituted alkylene, arylene, arylalkylene, and alkylarylene groups may be halogen atoms, cyano groups, pyridine groups, pyridinium groups, ether groups, aldehyde groups, ketone groups, ester groups, amide groups, carbonyl groups, thiocarbonyl groups, phosphine groups, phosphonium groups, phosphate groups, nitrile groups, mercaptosulfide groups, nitro groups, nitroso groups, acyl groups, acid anhydride groups, azide groups, azo groups, cyanato groups, urethane groups, urea groups, mixtures thereof, and the like, and wherein two or more substituents may be joined together to form a ring.

In some embodiments, $R_2$ is a $C_{16}$ to $C_{50}$ dimer acid (e.g., $C_{36}$ dimer acid), including a $C_{20}$ to $C_{50}$ dimer acid, $C_{24}$ to $C_{40}$ dimer acid, or $C_{30}$ to $C_{40}$ dimer acid. In some embodiments, $R_2$ is a dimer acid having the following structure:

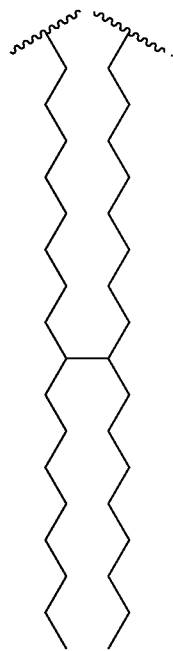 [SMILES: *CCCCCCCCC(CCCCCCCC)C(CCCCCCCC)CCCCCCCC*]

In embodiments, the gellant may be a compound with the following general structure:

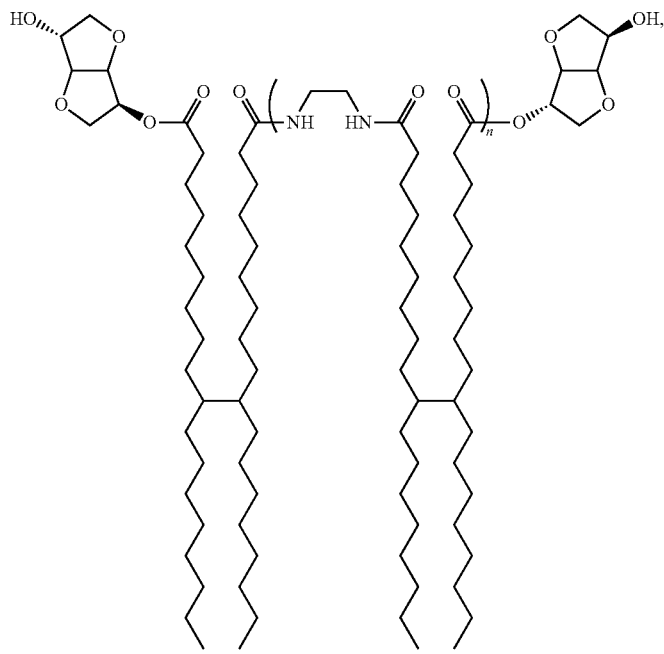

where n is 0 to 20. In some embodiments, n is 0, 1, 2, 3, 4, 5, 6, 7, 8, 9, 10, 11, 12, 13, 14, 15, 16, 17, 18, 19, or 20. In some embodiments, n is 0 to 10.

Figure 2:
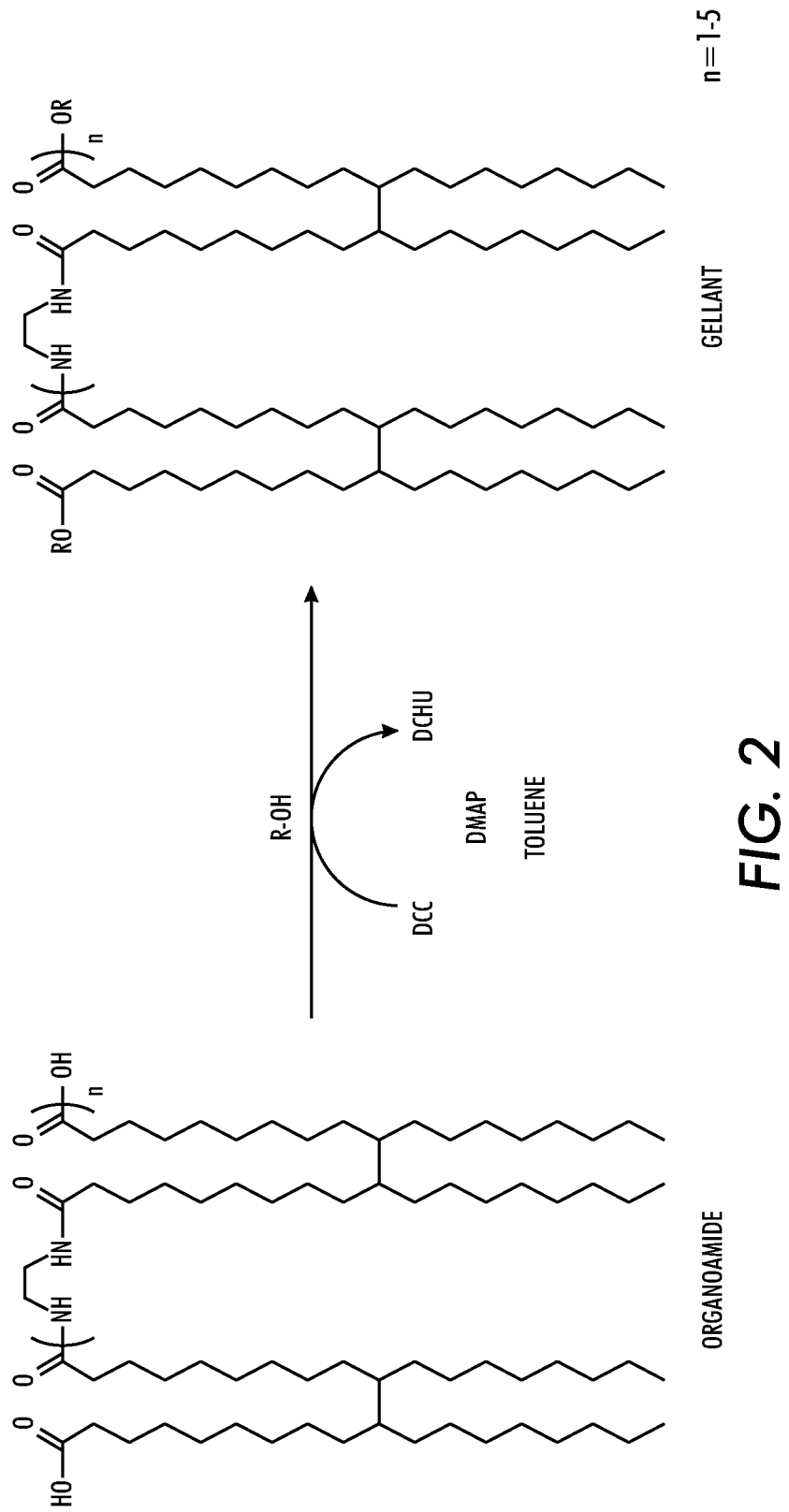
FIG. 2. Amide Gellant End-Capping Reaction with Alcohol.
Figure 3:
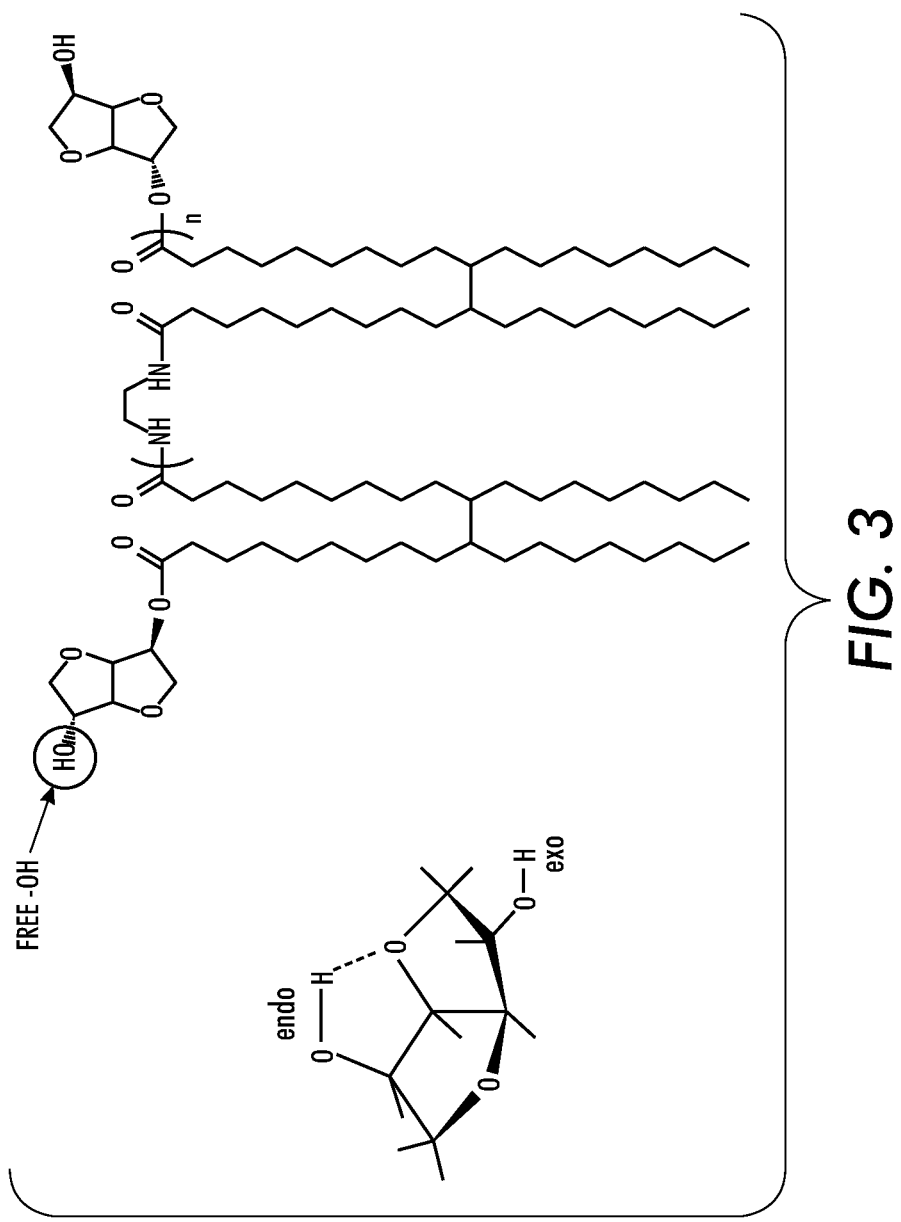
FIG. 3. Structure of Isosorbide and Isosorbide-Capped Gellant.

Isosorbide is a bio-based diol molecule derived from the acid-catalyzed cyclization of sorbitol, a sugar that is found in corn. Amide gellant end-capping is done by reacting the amide gellant precursor ('organoamide intermediate 1') with an alcohol using a DCC coupling reaction to form a diester (gellant) as shown in FIG. 2.

Due to isosorbide's unique V-shaped structure (two fused tetrahydrofuran rings), the two —OH groups have different reactivity (endo and exo-). Depending on the reaction conditions, either the endo- or exo-OH group can be functionalized. The added functionality of having an extra free —OH terminus on the gellant may provide further opportunities for hydrogen-bonding, and further functionalization if desired. This differing reactivity is unique to molecules like isosorbide, using other diols in the gellant synthesis can potentially lead to other undesired side products, such as dimers or oligomers. Thus, the amide gellants containing isosorbide of the present embodiments provide an example of a difunctional molecule where only one functional group participates in the esterification process under mild DCC coupling conditions.

Curable Inks

In some embodiments, the inks of the present embodiments contain an amide gellant that has been terminated ('end-capped') with isosorbide as set forth in FIG. 1. The present disclosure also relates to curable inks comprising an amide gellant of the present embodiments.

The ink can include the gelling agent, or gellant, in any suitable amount, such as about 1 percent to about 50 percent or from about 2 percent to about 20 percent or from about 5 percent to about 15 percent by weight of the ink.

In some embodiments, the ink compositions of the present embodiments may be solid inks. Solid ink technology broadens printing capability and customer base across many markets, and the diversity of printing applications will be facilitated by effective integration of printhead technology, print process and ink materials. The curable solid ink compositions are characterized by being solid at room temperature, for example, 20-50° C. or 20-27° C., and molten at an elevated temperature at which the molten ink is applied to a substrate. The ink compositions of the present embodiments may be solid curable inks at room temperature both in the presence and absence of a gellant.

In some embodiments, the ink compositions may further optionally comprise one or more of the following: curable waxes, monomers, colorants, and free-radical photoinitiators, and optionally up to 5 percent by weight of non-curable resins, such as viscosity modifiers.

The curable wax may be present in the curable solid ink in an amount of from about 0.1 to about 30% of the total weight of the curable solid ink. This includes from about 1% to about 30%, from about 5% to about 30%, from about 1% to about 20%, from about 5% to about 15%, and from about 5% to about 10% by weight of the ink.

In specific embodiments, the curable monomers may be present in the curable solid ink in an amount of from about 50 to about 95%, or from about 60 to about 90% by weight of the total weight of the curable solid ink. This includes from about 50% to about 80%, from about 50% to about 70%, from about 50% to about 70%, from about 60% to about 80%, from about 60% to about 70%, and from about 80% to about 95% by weight of the ink.

The gellant may be present in the curable solid ink in an amount of from about 1% to about 50%, from about 1% to about 30%, from about 2% to about 20%, from about 5% to about 15%, and from about 5% to about 10% by weight of the ink. In a specific embodiment, the gellant is present in the curable solid ink in an amount of about 7 percent by weight of the total weight of the curable solid ink.

The colorant may be present in the curable solid ink in an amount of from about 0.1% to about 10%, from about 1% to about 10%, from about 5% to about 10%, or from about 1% to about 5% by weight of the total weight of the curable solid ink.

The photoinitiator may be present in the curable solid ink in an amount of from about 0.5% to about 15%, from about 5% to about 15%, from about 1% to about 10%, from about 5% to about 10%, and from about 1% to about 5% by weight of the total weight of the curable solid ink.

The ink compositions can be prepared by any desired or suitable method. For example, each of the components of the ink carrier can be mixed together, followed by heating, the mixture to at least its melting point, for example from about 60° C. to about 110° C., 80° C. to about 100° C. and 85° C. to about 95° C. The colorant may be added before the ink ingredients have been heated or after the ink ingredients have been heated. When pigments are the selected colorants, the molten mixture may be subjected to grinding in an attritor or ball mill apparatus to effect dispersion of the pigment in the ink carrier. The heated mixture is then stirred for about 5 seconds to about 30 minutes or more, to obtain a substantially homogeneous, uniform melt, followed by cooling the ink to ambient temperature (typically from about 20° C. to about 25° C.). The inks are solid at ambient temperature. In a specific embodiment, during the formation process, the inks in their molten state are poured into molds and then allowed to cool and solidify to form ink sticks. Suitable ink preparation techniques are disclosed in U.S. Pat. No. 7,186,762, the disclosure of which is incorporated herein by reference in its entirety.

The ink compositions of the present embodiments may further optionally include one or more conventional additives to take advantage of the known functionality associated with such conventional additives. Such additives may include, for example, at least one isocyanate derived material, antioxidant, defoamer, slip and leveling agents, clarifier, viscosity modifier, adhesive, plasticizer and the like. When present, the optional additives may each, or in combination, be present in the ink in any desired or effective amount, such as from about 1% to about 10%, from about 5% to about 10%, or from about 3% to about 5% by weight of the ink.

According to some embodiments, there is provided a curable solid ink comprising a gellant, wherein the gellant is an ester-terminated polyamide resin end-capped with isosorbide.

According to some embodiments, there is provided a curable solid ink comprising a curable wax; one or more monomers; an optional colorant; an amide gellant, wherein the gellant is an ester-terminated polyamide resin end-capped with isosorbide; and a photoinitiator.

In some embodiments, the ink compositions comprise at least one curable wax, at least one monomer and at least one isosorbide end-capped amide gellant disclosed herein. The ink compositions may optionally comprise one or more of the following: a non-curable component; a colorant; and a photoinitiator.

According to some embodiments, there is provided a curable solid ink comprising a curable wax; an optional non-curable component; one or more monomers; an optional colorant; an amide gellant, wherein the gellant is an ester-terminated polyamide resin end-capped with isosorbide; and a photoinitiator.

In some embodiments, the ink compositions of the present embodiments may be liquid curable inks. In some embodiments, the ink compositions of the present embodiments may further comprise additional gellants, which includes both curable and non-curable gellants.

Curable Waxes

The inks of the present embodiments may comprise blends of curable waxes, monomers, gellants, optional colorants, and free-radical photoinitiators, and optionally up to 5 percent by weight of non-curable resins, such as viscosity modifiers. The curable waxes, monomers, curable waxes, optional colorants, and free-radical photoinitiators are solid materials below about 40° C., or from below about 40° C. to below about 30° C., with little or no smell. These components were selected to achieve jetting at temperatures in the range of from about 70° C. to about 100° C., or from about 80° C. to about 100° C., or from about 70° C. to about 90° C. These solid inks thus have robust jetting at elevated temperatures with a viscosity of from about 5 to about 15 cPs, or from about 10 to about 15 cPs, or from about 8 to about 12 cPs at these temperatures, and are solid at room temperature which prevents excessive spreading or migration of the printed droplet on porous substrate. After printing, the compositions are cured to provide robust images.

The curable solid inks of the present embodiments have a pre-cured hardness of from about 0.1 to about 11 or of from about 0.1 to about 5, or of from about 0.1 to about 3. These inks have a post-cured hardness of from about 85 to about 100, or of from about 90 to about 97, or of from about 93 to about 97. The curable solid components include monomers, curable waxes and gellants. The curable wax may be a solid at room temperature (25° C.). Inclusion of the wax may promote an increase in viscosity of the ink composition as the composition cools from the application temperature. The curable wax may be any wax component that is miscible with the other components and that will polymerize to form a polymer. The term wax includes, for example, any of the various natural, modified natural, and synthetic materials commonly referred to as waxes.

Suitable examples of curable waxes include waxes that include or are functionalized with curable groups. The curable groups may include, for example, an acrylate, methacrylate, alkene, allylic ether, epoxide, oxetane, and the like. These waxes can be synthesized by the reaction of a wax, such as a polyethylene wax equipped with a carboxylic acid or hydroxyl transformable functional group.

Suitable examples of hydroxyl-terminated polyethylene waxes that may be functionalized with a curable group include mixtures of carbon chains with the structure $CH_3$—$(CH_2)_n$—$CH_2OH$, where there is a mixture of chain lengths, n, where the average chain length can be in the range of about 16 to about 50, and linear low molecular weight polyethylene, of similar average chain length. Suitable examples of such waxes include, but are not limited to, the UNILIN series of materials such as UNILIN 350, UNILIN 425, UNILIN 550 and UNILIN 700 with $M_n$ approximately equal to 375, 460, 550 and 700 g/mol, respectively. All of these waxes are commercially available from Baker-Petrolite. Guerbet alcohols, characterized as 2,2-dialkyl-1-ethanols, are also suitable compounds. Exemplary Guerbet alcohols include those containing about 16 to about 36 carbons, many of which are commercially available from Jarchem Industries Inc., Newark, N.J. PRIPOL® 2033 (C-36 dimer diol mixture including isomers of the formula

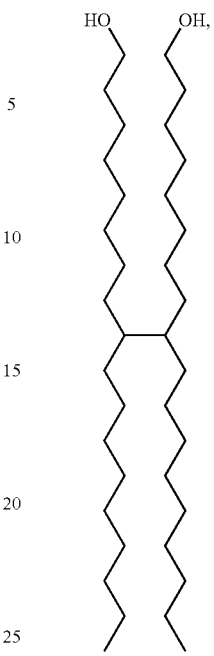

as well as other branched isomers that may include unsaturations and cyclic groups, available from Uniqema, New Castle, Del.; further information on $C_{36}$ dimer diols of this type is disclosed in, for example, "Dimer Acids," *Kirk-Othmer Encyclopedia of Chemical Technology*, Vol. 8, 4th Ed. (1992), pp. 223-237, the disclosure of which is totally incorporated herein by reference, may also be used. These alcohols can be reacted with carboxylic acids equipped with UV curable moieties to form reactive esters. Examples of these acids include acrylic and methacrylic acids, available from Sigma-Aldrich Co.

Suitable examples of carboxylic acid-terminated polyethylene waxes that may be functionalized with a curable group include mixtures of carbon chains with the structure $CH_3$—$(CH_2)_n$—$COOH$, where there is a mixture of chain lengths, n, where the average chain length is about 16 to about 50, and linear low molecular weight polyethylene, of similar average chain length. Suitable examples of such waxes include UNICID® 350, UNICID® 425, UNICID® 550 and UNICID® 700 with $M_n$ equal to approximately 390, 475, 565 and 720 g/mol, respectively. Other suitable waxes have a structure $CH_3$—$(CH_2)_n$—$COOH$, such as hexadecanoic or palmitic acid with n=14, heptadecanoic or margaric or daturic acid with n=15, octadecanoic or stearic acid with n=16, eicosanoic or arachidic acid with n=18, docosanoic or behenic acid with n=20, tetracosanoic or lignoceric acid with n=22, hexacosanoic or cerotic acid with n=24, heptacosanoic or carboceric acid with n=25, octacosanoic or montanic acid with n=26, triacontanoic or melissic acid with n=28, dotriacontanoic or lacceroic acid with n=30, tritriacontanoic or ceromelissic or psyllic acid, with n=31, tetratriacontanoic or geddic acid with n=32, pentatriacontanoic or ceroplastic acid with n=33. Guerbet acids, characterized as 2,2-dialkyl ethanoic acids, are also suitable compounds. Exemplary Guerbet acids include those containing 16 to 36 carbons, many of which are commercially available from Jarchem Industries Inc., Newark, N.J. PRIPOL® 1009 (C-36 dimer acid mixture including isomers of the formula

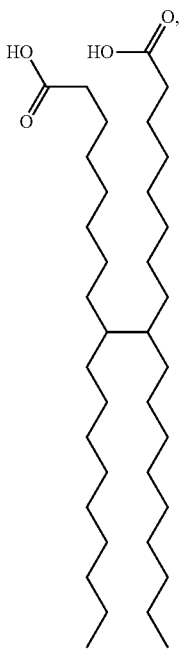 [SMILES: CCCCCCCCCC(CCCCCCCC(=O)O)C(CCCCCCCCC)CCCCCCCC(=O)O]

as well as other branched isomers that may include unsaturations and cyclic groups, available from Uniqema, New Castle, Del.; further information on $C_{36}$ dimer acids of this type is disclosed in, for example, "Dimer Acids," *Kirk-Othmer Encyclopedia of Chemical Technology*, Vol. 8, 4th Ed. (1992), pp. 223-237, the disclosure of which is totally incorporated herein by reference, can also be used. These carboxylic acids can be reacted with alcohols equipped with UV curable moieties to form reactive esters. Examples of these alcohols include, but are not limited to, 2-allyloxyethanol from Sigma-Aldrich Co.;

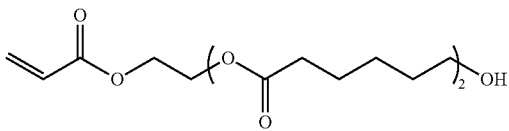

SR495B from Sartomer Company, Inc. (Exton, Pennsylvannia); and

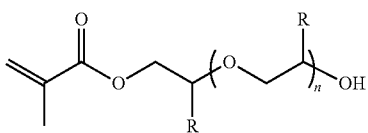

CD572 (R═H, n=10) and SR604 (R═Me, n=4) from Sartomer Company, Inc.

The curable wax can be included in the composition in an amount of from, for example, about 0.1% to about 30% by weight of the composition, such as from about 0.5% to about 20% or from about 0.5% to 15% by weight of the composition.

Monomers

In some embodiments, the ink compositions may further optionally comprise monomers. The monomers that may be used in the present embodiments are, in embodiments, those described in U.S. Pat. No. 7,559,639, which is hereby incorporated by reference. For example, the monomer may be a dimethanol diacrylate cyclohexane difunctional monomer, such as for example, CD-406 from Sartomer (mp=78° C.); an isocyanurate triacrylate trifunctional monomer, such as for example, SR-368 from Sartomer (mp=50-55° C.); a behenyl acrylate monofunctional monomer C18, C20, C22 mixture, such as for example, CD587 from Sartomer (mp=55° C.); an acrylate curable monofunctional acrylate wax C22, C23, C24 mixture, such as for example, UNILIN 350 from Baker Petrolite (Houston, Tex.) (mp=78-83° C.); and a curable amide gellant.

In some embodiments, the monomer is a curable monomer. Thus, ink of the present embodiments may comprise at least a isosorbide end-capped amide gellant, at least a curable wax, an optional photoinitiator, an optional colorant, and at least a curable monomer. In embodiments, if more than one curable liquid monomer is present in the curable phase change ink, the curable liquid monomers are referred to "co-monomers". The co-monomers may be chosen from any suitable curable monomers.

Ink compositions of embodiments may comprise a first co-monomer, due to the solubility and gelling properties of gellant materials, such as, epoxy-polyamide composite gellants, which are useful for producing ink compositions including an ink vehicle having a thermally-driven and reversible gel phase, where the ink vehicle is comprised of curable liquid monomers, such as UV-curable liquid monomers. The gel phase of such ink compositions allows an ink droplet to be pinned to a receiving substrate.

Examples of the at least one curable monomer of the composition include propoxylated neopentyl glycol diacrylate (such as SR9003 from Sartomer), diethylene glycol diacrylate, triethylene glycol diacrylate, butanediol diacrylate, hexanediol diacrylate, dipropyleneglycol diacrylate, tripropylene glycol diacrylate, alkoxylated neopentyl glycol diacrylate, isodecyl acrylate, tridecyl acrylate, isobornyl acrylate, isobornyl(meth)acrylate, propoxylated trimethylolpropane triacrylate, ethoxylated trimethylolpropane triacrylate, di-trimethylolpropane tetraacrylate, dipentaerythritol pentaacrylate, ethoxylated pentaerythritol tetraacrylate, propoxylated glycerol triacrylate, isobornyl methacrylate, lauryl acrylate, lauryl methacrylate, neopentyl glycol propoxylate methylether monoacrylate, isodecylmethacrylate, caprolactone acrylate, 2-phenoxyethyl acrylate, isooctylacrylate, isooctylmethacrylate, tricyclodecane dimethanol diacrylate, dioxane glycol diacrylate, mixtures thereof and the like. As relatively non-polar monomers, mention may be made of isodecyl(meth)acrylate, caprolactone acrylate, 2-phenoxyethyl acrylate, isooctyl(meth)acrylate, and butyl acrylate. In addition, multifunctional acrylate monomers/oligomers may be used not only as reactive diluents, but also as materials that can increase the cross-link density of the cured image, thereby enhancing the toughness of the cured images.

The term "curable monomer" is also intended to encompass curable oligomers, which may also be used in the composition. Examples of suitable curable oligomers that may be used in the compositions have a low viscosity, for example, from about 50 cPs to about 10,000 cPs, such as from about 75 cPs to about 7,500 cPs or from about 100 cPs to about 5,000 cPs. Examples of such oligomers may include CN549, CN131, CN131B, CN2285, CN 3100, CN3105, CN132, CN133, CN 132, available from Sartomer Company, Inc., Exeter, Pa., Ebecryl 140, Ebecryl 1140, Ebecryl 40, Ebecryl 3200, Ebecryl 3201, Ebecryl 3212, available from Cytec Industries Inc, Smyrna Ga., PHOTOMER 3660, PHO- TOMER 5006F, PHOTOMER 5429, PHOTOMER 5429F, available from Cognis Corporation, Cincinnati, Ohio, LAROMER PO 33F, LAROMER PO 43F, LAROMER PO 94F, LAROMER UO 35D, LAROMER PA 9039V, LAROMER PO 9026V, LAROMER 8996, LAROMER 8765, LAROMER 8986, available from BASF Corporation, Florham Park, N.J., and the like. As multifunctional acrylates and methacrylates, mention may also be made of pentaerythritol tetra(meth)acrylate, 1,2 ethylene glycol di(meth)acrylate, 1,6 hexanediol di(meth)acrylate, 1,12-dodecanol di(meth)acrylate, tris(2-hydroxy ethyl)isocyanurate triacrylate, propoxylated neopentyl glycol diacrylate, hexanediol diacrylate, tripropylene glycol diacrylate, dipropylene glycol diacrylate, amine-modified polyether acrylates (available as PO 83 F, LR 8869, and/or LR 8889 (all available from BASF Corporation)), trimethylolpropane triacrylate, glycerol propoxylate triacrylate, dipentaerythritol penta-/hexa-acrylate, ethoxylated pentaerythritol tetraacrylate (available from Sartomer Co. Inc. as SR399LV and SR 494), and the like.

Additional examples of the curable monomers include acrylated esters, acrylated polyesters, acrylated ethers, acrylated polyethers, acrylated epoxies, urethane acrylates, and pentaerythritol tetraacrylate. Specific examples of suitable acrylated oligomers include, acrylated polyester oligomers, such as CN2262 (Sartomer Co.), EB 812 (Cytec Surface Specialties), EB 810 (Cytec Surface Specialties), CN2200 (Sartomer Co.), CN2300 (Sartomer Co.), and the like; acrylated urethane oligomers, such as EB270 (UCB Chemicals), EB 5129 (Cytec Surface Specialties), CN2920 (Sartomer Co.), CN3211 (Sartomer Co.), and the like; and acrylated epoxy oligomers, such as EB 600 (Cytec Surface Specialties), EB 3411 (Cytec Surface Specialties), CN2204 (Sartomer Co.), CN110 (Sartomer Co.), and the like.

In embodiments, the curable monomer may be chosen from short-chain alkyl glycol diacrylates or ether diacrylates or from acrylates having short-chain alkyl ester substituents, such as caprolactone acrylate, and the commercially available products CD536, CD 2777, CD585 and CD586 (available from Sartomer Co. Inc.).

In addition, the curable monomer or oligomer may variously function as a viscosity reducer, as a binder when the composition is cured, as an adhesion promoter, as a reactive diluent and as a crosslinking agent that can increase the crosslink density of the cured image, thereby enhancing the toughness of the cured images. Suitable monomers may have a low molecular weight, low viscosity, and low surface tension and comprise functional groups that undergo polymerization upon exposure to radiation such as UV light.

As mentioned above, the one or more monomers may be present in the ink in an amount of, for example, about 10 to about 90% by weight of the ink, such as about 20 to about 80% by weight of the ink, or about 50 to about 70% by weight of the total ink composition although the amounts can be outside of these ranges.

Initiator

In some embodiments, the ink compositions may further optionally comprise an initiator, such as, for example, a photoinitiator. Such an initiator is desirable for assisting in curing of the ink. In embodiments, a photoinitiator that absorbs radiation, for example UV light radiation, to initiate curing of the curable components of the ink may be used. As the photoinitiator for ink compositions that are cured by free-radical polymerization, for instance, ink compositions containing acrylate groups or inks comprised of polyamides, mention may be made of photoinitiators such as benzophenones, benzoin ethers, benzil ketals, α-hydroxyalkylphenones, α-alkoxyalkylphenones α-aminoalkylphenones and acylphosphine photoinitiators sold under the trade designations of IRGACURE and DAROCUR from Ciba. Specific examples of suitable photoinitiators include 2,4,6-trimethylbenzoyldiphenylphosphine oxide (available as BASF LUCIRIN TPO); 2,4,6-trimethylbenzoylethoxyphenylphosphine oxide (available as BASF LUCIRIN TPO-L); bis(2,4,6-trimethylbenzoyl)-phenyl-phosphine oxide (available as Ciba IRGACURE 819) and other acyl phosphines; 2-methyl-1-(4-methylthio)phenyl-2-(4-morphorlinyl)-1-propanone (available as Ciba IRGACURE 907) and 1-(4-(2-hydroxyethoxy)phenyl)-2-hydroxy-2-methylpropan-1-one (available as Ciba IRGACURE 2959); 2-benzyl 2-dimethylamino 1-(4-morpholinophenyl)butanone-1 (available as Ciba IRGACURE 369); 2-hydroxy-1-(4-(4-(2-hydroxy-2-methylpropionyl)-benzyl)-phenyl)-2-methylpropan-1-one (available as Ciba IRGACURE 127); 2-dimethylamino-2-(4-methylbenzyl)-1-(4-morpholin-4-ylphenyl)-butanone (available as Ciba IRGACURE 379); titanocenes; isopropylthioxanthone; 1-hydroxy-cyclohexylphenylketone; benzophenone; 2,4,6-trimethylbenzophenone; 4-methylbenzophenone; diphenyl-(2,4,6-trimethylbenzoyl)phosphine oxide; 2,4,6-trimethylbenzoylphenylphosphinic acid ethyl ester; oligo(2-hydroxy-2-methyl-1-(4-(1-methylvinyl)phenyl)propanone); 2-hydroxy-2-methyl-1-phenyl-1-propanone; benzyl-dimethylketal; and mixtures thereof. Mention may also be made of amine synergists, which are described as co-initiators that donate a hydrogen atom to a photoinitiator and thereby form a radical species that initiates polymerization (amine synergists can also consume oxygen dissolved in the ink—as oxygen inhibits free-radical polymerization its consumption increases the speed of polymerization), for example such as ethyl-4-dimethylaminobenzoate and 2-ethylhexyl-4-dimethylaminobenzoate. This list is not exhaustive, and any known photoinitiator that initiates the free-radical reaction upon exposure to a desired wavelength of radiation such as UV light can be used without limitation.

The photoinitiator may absorb radiation of about 200 to about 420 nm wavelengths in order to initiate cure, although use of initiators that absorb at longer wavelengths, such as the titanocenes that may absorb up to 560 nm, can also be used without restriction.

The total amount of initiator included in the ink composition may be from, for example, about 0.5 to about 15% by weight, such as from about 1 to about 10% by weight, of the ink composition.

Radiation curable phase change inks generally comprise at least one curable monomer, a gellator, a colorant, and a radiation activated initiator, specifically a photoinitiator, that initiates polymerization of curable components of the ink, specifically of the curable monomer. U.S. Pat. No. 7,279,587 to Odell et al., the disclosure of which is totally incorporated herein by reference, discloses photoinitiating compounds useful in curable solid ink compositions. U.S. Patent Publication 2007/0120910 to Odell et al., which is hereby incorporated by reference herein in its entirety, describes, in embodiments, a solid ink comprising a colorant, an initiator, and an ink vehicle.

Optionally, the ink compositions can also contain an amine synergist, which are co-initiators which can donate a hydrogen atom to a photoinitiator and thereby form a radical species that initiates polymerization, and can also consume dissolved oxygen, which inhibits free-radical polymerization, thereby increasing the speed of polymerization. Examples of suitable amine synergists include (but are not limited to) ethyl-4-dimethylaminobenzoate, 2-ethylhexyl-4-dimethylaminobenzoate, and the like, as well as mixtures thereof.

Initiators for inks disclosed herein can absorb radiation at any desired or effective wavelength, for example, from about 4 nanometers to about 560 nanometers, or from about 200 nanometers to about 560 nanometers, or from about 200 nanometers to about 420 nanometers, although the wavelength can be outside of these ranges.

Optionally, the photoinitiator is present in the phase change ink in any desired or effective amount, for example from about 0.5 percent to about 15 percent by weight of the ink composition, or from about 1 percent to about 10 percent by weight of the ink composition, although the amount can be outside of these ranges.

Colorant

In some embodiments, the ink compositions may further optionally comprise colorant. Any desired or effective colorant can be employed in the ink compositions, including dyes, pigments, mixtures thereof, and the like, provided that the colorant can be dissolved or dispersed in the ink vehicle and is compatible with the other ink components. Pigments, which are typically cheaper and more robust than dyes, may be included in the curable phase change ink composition. The color of many dyes can be altered by the polymerization process occurring during the curing stage, presumably from attack of their molecular structure by the free radicals. The compositions can be used in combination with conventional ink-colorant materials, such as Color Index (C.I.) Solvent Dyes, Disperse Dyes, modified Acid and Direct Dyes, Basic Dyes, Sulphur Dyes, Vat Dyes, and the like.

Examples of suitable dyes include Neozapon Red 492 (BASF); Orasol Red G (Ciba); Direct Brilliant Pink B (Oriental Giant Dyes); Direct Red 3BL (Classic Dyestuffs); Supranol Brilliant Red 3BW (Bayer AG); Lemon Yellow 6G (United Chemie); Light Fast Yellow 3G (Shaanxi); Aizen Spilon Yellow C-GNH (Hodogaya Chemical); Bernachrome Yellow GD Sub (Classic Dyestuffs); Cartasol Brilliant Yellow 4GF (Clariant); Cibanon Yellow 2GN (Ciba); Orasol Black CN (Ciba); Savinyl Black RLSN (Clariant); Pyrazol Black BG (Clariant); Morfast Black 101 (Rohm & Haas); Diaazol Black RN (ICI); Orasol Blue GN (Ciba); Savinyl Blue GLS (Clariant); Luxol Fast Blue MBSN (Pylam Products); Sevron Blue 5GMF (Classic Dyestuffs); Basacid Blue 750 (BASF), Neozapon Black X51 (BASF), Classic Solvent Black 7 (Classic Dyestuffs), Sudan Blue 670 (C.I. 61554) (BASF), Sudan Yellow 146 (C.I. 12700) (BASF), Sudan Red 462 (C.I. 26050) (BASF), C.I. Disperse Yellow 238, Neptune Red Base NB543 (BASF, C.I. Solvent Red 49), Neopen Blue FF-4012 from BASF, Lampronol Black BR from ICI (C.I. Solvent Black 35), Morton Morplas Magenta 36 (C.I. Solvent Red 172), metal phthalocyanine colorants such as those disclosed in U.S. Pat. No. 6,221,137, the disclosure of which is totally incorporated herein by reference, and the like. Polymeric dyes can also be used, such as those disclosed in, for example, U.S. Pat. No. 5,621,022 and U.S. Pat. No. 5,231,135, the disclosures of each of which are herein entirely incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactant Orange X-38, uncut Reactant Blue X-17, Solvent Yellow 162, Acid Red 52, Solvent Blue 44, and uncut Reactant Violet X-80.

Pigments are also suitable colorants for the curable phase change inks. Examples of suitable pigments include PALIOGEN Violet 5100 (commercially available from BASF); PALIOGEN Violet 5890 (commercially available from BASF); HELIOGEN Green L8730 (commercially available from BASF); LITHOL Scarlet D3700 (commercially available from BASF); SUNFAST Blue 15:4 (commercially available from Sun Chemical); Hostaperm Blue B2G-D (commercially available from Clariant); Hostaperm Blue B4G (commercially available from Clariant); Permanent Red P-F7RK; Hostaperm Violet BL (commercially available from Clariant); LITHOL Scarlet 4440 (commercially available from BASF); Bon Red C (commercially available from Dominion Color Company); ORACET Pink RF (commercially available from Ciba); PALIOGEN Red 3871 K (commercially available from BASF); SUNFAST Blue 15:3 (commercially available from Sun Chemical); PALIOGEN Red 3340 (commercially available from BASF); SUNFAST Carbazole Violet 23 (commercially available from Sun Chemical); LITHOL Fast Scarlet L4300 (commercially available from BASF); SUNBRITE Yellow 17 (commercially available from Sun Chemical); HELIOGEN Blue L6900, L7020 (commercially available from BASF); SUNBRITE Yellow 74 (commercially available from Sun Chemical); SPECTRA PAC C Orange 16 (commercially available from Sun Chemical); HELIOGEN Blue K6902, K6910 (commercially available from BASF); SUNFAST Magenta 122 (commercially available from Sun Chemical); HELIOGEN Blue D6840, D7080 (commercially available from BASF); Sudan Blue OS (commercially available from BASF); NEOPEN Blue FF4012 (commercially available from BASF); PV Fast Blue B2GO1 (commercially available from Clariant); IRGALITE Blue BCA (commercially available from Ciba); PALIOGEN Blue 6470 (commercially available from BASF); Sudan Orange G (commercially available from Aldrich), Sudan Orange 220 (commercially available from BASF); PALIOGEN Orange 3040 (BASF); PALIOGEN Yellow 152, 1560 (commercially available from BASF); LITHOL Fast Yellow 0991K (commercially available from BASF); PALIOTOL Yellow 1840 (commercially available from BASF); NOVOPERM Yellow FGL (commercially available from Clariant); Ink Jet Yellow 4G VP2532 (commercially available from Clariant); Toner Yellow HG (commercially available from Clariant); Lumogen Yellow D0790 (commercially available from BASF); Suco-Yellow L1250 (commercially available from BASF); Suco-Yellow D1355 (commercially available from BASF); Suco Fast Yellow D1355, D1351 (commercially available from BASF); HOSTAPERM Pink E 02 (commercially available from Clariant); Hansa Brilliant Yellow 5GX03 (commercially available from Clariant); Permanent Yellow GRL 02 (commercially available from Clariant); Permanent Rubine L6B 05 (commercially available from Clariant); FANAL Pink D4830 (commercially available from BASF); CINQUASIA Magenta (commercially available from DU PONT); PALIOGEN Black L0084 (commercially available from BASF); Pigment Black K801 (commercially available from BASF); and carbon blacks such as REGAL 330™ (commercially available from Cabot), Nipex 150 (commercially available from Degusssa) Carbon Black 5250 and Carbon Black 5750 (commercially available from Columbia Chemical), and the like, as well as mixtures thereof.

Also suitable are the colorants disclosed in U.S. Pat. No. 6,472,523, U.S. Pat. No. 6,726,755, U.S. Pat. No. 6,476,219, U.S. Pat. No. 6,576,747, U.S. Pat. No. 6,713,614, U.S. Pat. No. 6,663,703, U.S. Pat. No. 6,755,902, U.S. Pat. No. 6,590,082, U.S. Pat. No. 6,696,552, U.S. Pat. No. 6,576,748, U.S. Pat. No. 6,646,111, U.S. Pat. No. 6,673,139, U.S. Pat. No. 6,958,406, U.S. Pat. No. 6,821,327, U.S. Pat. No. 7,053,227, U.S. Pat. No. 7,381,831 and U.S. Pat. No. 7,427,323, the disclosures of each of which are incorporated herein by reference in their entirety.

In embodiments, solvent dyes are employed. An example of a solvent dye suitable for use herein may include spirit soluble dyes because of their compatibility with the ink carriers disclosed herein. Examples of suitable spirit solvent dyes include Neozapon Red 492 (BASF); Orasol Red G (Ciba); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH (Hodogaya Chemical); Cartasol Brilliant Yellow 4GF (Clariant); Pergasol Yellow CGP (Ciba); Orasol Black RLP (Ciba); Savinyl Black RLS (Clariant); Morfast Black Conc. A (Rohm and Haas); Orasol Blue GN (Ciba); Savinyl Blue GLS (Sandoz); Luxol Fast Blue MBSN (Pylam); Sevron Blue 5GMF (Classic Dyestuffs); Basacid Blue 750 (BASF); Neozapon Black X51 [C.I. Solvent Black, C.I. 12195] (BASF), Sudan Blue 670 [C.I. 61554] (BASF), Sudan Yellow 146 [C.I. 12700] (BASF), Sudan Red 462 [C.I. 260501] (BASF), mixtures thereof and the like.

The colorant may be present in the ink in any desired or effective amount to obtain the desired color or hue such as, for example, at least from about 0.1 percent by weight of the ink to about 50 percent by weight of the ink, or from at least from about 0.2 percent by weight of the ink to about 20 percent by weight of the ink, or at least from about 0.5 percent by weight of the ink to about 10 percent by weight of the ink.

Ink Vehicle or Carrier

In specific embodiments, the ink vehicles disclosed herein can comprise any suitable curable monomer or prepolymer. The curable monomer or prepolymer and curable wax together can form more than about 50 percent, or at least 70 percent, or at least 80 percent by weight of the ink. Examples of suitable materials include radically curable monomer compounds, such as acrylate and methacrylate monomer compounds, which are suitable for use as phase change ink carriers. Specific examples of relatively nonpolar acrylate and methacrylate monomers include (but are not limited to) isobornyl acrylate, isobornyl methacrylate, lauryl acrylate, lauryl methacrylate, isodecylacrylate, isodecylmethacrylate, caprolactone acrylate, 2-phenoxyethyl acrylate, isooctylacrylate, isooctylmethacrylate, butyl acrylate, and the like, as well as mixtures and combinations thereof. In addition, multifunctional acrylate and methacrylate monomers and oligomers can be included in the phase change ink carrier as reactive diluents and as materials that can increase the crosslink density of the cured image, thereby enhancing the toughness of the cured images. Examples of suitable multifunctional acrylate and methacrylate monomers and oligomers include (but are not limited to) pentaerythritol tetraacrylate, pentaerythritol tetramethacrylate, 1,2-ethylene glycol diacrylate, 1,2-ethylene glycol dimethacrylate, 1,6-hexanediol diacrylate, 1,6-hexanediol dimethacrylate, 1,12-dodecanol diacrylate, 1,12-dodecanol dimethacrylate, tris(2-hydroxy ethyl)isocyanurate triacrylate, propoxylated neopentyl glycol diacrylate (available from Sartomer Co. Inc. as SR 9003), hexanediol diacrylate, tripropylene glycol diacrylate, dipropylene glycol diacrylate, amine modified polyether acrylates (available as PO 83 F, LR 8869, and/or LR 8889 (all available from BASF Corporation), trimethylolpropane triacrylate, glycerol propoxylate triacrylate, dipentaerythritol pentaacrylate, dipentaerythritol hexaacrylate, ethoxylated pentaerythritol tetraacrylate (available from Sartomer Co. Inc. as SR 494), and the like, as well as mixtures and combinations thereof. When a reactive diluent is added to the ink carrier material, the reactive diluent is added in any desired or effective amount, for example, from about 1 percent to about 80 percent by weight of the carrier, or from about 35 percent to about 70 percent by weight of the carrier, although the amount of diluent can be outside of these ranges.

In specific embodiments, the ink vehicles disclosed herein can comprise any suitable photoinitiator. Examples of specific initiators include, but are not limited to, IRGACURE® 127, IRGACURE® 379, and IRGACURE® 819, all commercially available from Ciba Specialty Chemicals, among others. Further examples of suitable initiators include (but are not limited to) benzophenones, benzophenone derivatives, benzyl ketones, α-alkoxy benzyl ketones, monomeric hydroxyl ketones, polymeric hydroxyl ketones, α-amino ketones, alkoxy ketones, acyl phosphine oxides, metallocenes, benzoin ethers, benzil ketals, α-hydroxyalkylphenones, α-aminoalkylphenones, acylphosphine photoinitiators sold under the trade designations of IRGACURE® and DAROCUR® from Ciba, and the like. Specific examples include 1-hydroxy-cyclohexylphenyl ketone, benzophenone, 2-benzyl-2-(dimethylamino)-1-(4-(4-morphorlinyl)phenyl)-1-butanone, 2-methyl-1-(4-methylthio)phenyl-2-(4-morphorlinyl)-1-propanone, diphenyl-(2,4,6-trimethylbenzoyl)phosphine oxide, phenyl bis(2,4,6-trimethylbenzoyl)phosphine oxide, benzyl-dimethylketal, isopropylthioxanthone, 2,4,6-trimethylbenzoyldiphenylphosphine oxide (available as BASF LUCIRIN® TPO), 2,4,6-trimethylbenzoylethoxyphenylphosphine oxide (available as BASF LUCIRIN® TPO-L), bis(2,4,6-trimethylbenzoyl)-phenyl-phosphine oxide (available as Ciba IRGACURE® 819) and other acyl phosphines, 2-methyl-1-(4-methylthio)phenyl-2-(4-morphorlinyl)-1-propanone (available as Ciba IRGACURE® 907) and 1-(4-(2-hydroxyethoxy)phenyl)-2-hydroxy-2-methylpropan-1-one (available as Ciba IRGACURE® 2959), 2-benzyl 2-dimethylamino-1-(4-morpholinophenyl) butanone-1 (available as Ciba IRGACURE® 369), 2-hydroxy-1-(4-(4-(2-hydroxy-2-methylpropionyl)-benzyl)-phenyl-2-methylpropan-1-one (available as Ciba IRGACURE® 127), 2-dimethylamino-2-(4-methylbenzyl)-1-(4-morpholin-4-ylphenyl)-butanone (available as Ciba IRGACURE® 379), titanocenes, isopropylthioxanthone, 1-hydroxy-cyclohexylphenylketone, benzophenone, 2,4,6-trimethylbenzophenone, 4-methylbenzophenone, diphenyl-(2,4,6-trimethylbenzoyl)phosphine oxide, 2,4,6-trimethylbenzoylphenylphosphinic acid ethyl ester, oligo(2-hydroxy-2-methyl-1-(4-(1-methylvinyl)phenyl)propanone), 2-hydroxy-2-methyl-1-phenyl-1-propanone, benzyl-dimethylketal, arylsulphonium slats, aryl iodonium salt, and the like, as well as mixtures thereof.

Methods of Use

According to some embodiments, methods are provided for using the curable solid ink for jet printing text. In such embodiments, the method comprises jetting a curable solid ink onto an intermediate substrate to form an intermediate image, transferring the intermediate image onto a substrate to form a transferred image, and exposing the transferred image to radiation having wavelengths in the range of from about 180 nanometers to about 500 nanometers to cure the curable solid ink. In embodiments, the jetting step is performed at above 70° C., or at from about 70 to about 100° C.

Any suitable printing device may used herein. In one embodiment, the apparatus is an ink jet printing device as described in commonly assigned, co-pending U.S. Patent Publication No. 2008/0218540, incorporated by reference in its entirety, that includes at least an ink jet print head and a print region surface toward which ink is jetted from the ink jet print head, wherein a height distance between the ink jet print head and the print region surface is adjustable.

The apparatus, as well as the methods herein, may be employed with any desired printing system and marking material suitable for applying a marking material in an imagewise pattern to an intermediate transfer member or directly to an image receiving substrate, piezoelectric ink jet printing (both with inks liquid at room temperature and with phase change inks), acoustic ink jet printing (both with inks liquid at room temperature and with phase change inks), thermal transfer printing, gravure printing, and the like. For the purpose of illustration, a piezoelectric phase change ink jet printer for applying marking material in an imagewise pattern to an intermediate transfer member is described.

The inks can be employed in apparatus for direct printing ink jet processes and in indirect (offset) printing ink jet applications. Another embodiment disclosed herein is directed to a process which comprises incorporating an ink as disclosed herein into an ink jet printing apparatus, melting the ink, and causing droplets of the melted ink to be ejected in an imagewise pattern onto a recording substrate. A direct printing process is also disclosed in, for example, U.S. Pat. No. 5,195,430, the disclosure of which is totally incorporated herein by reference. Yet another embodiment disclosed herein is directed to a process which comprises incorporating an ink as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. In another specific embodiment, both the intermediate transfer member and the final recording sheet are heated; in this embodiment, both the intermediate transfer member and the final recording sheet are heated to a temperature below that of the melted ink in the printing apparatus; in this embodiment, the relative temperatures of the intermediate transfer member and the final recording sheet can be (1) the intermediate transfer member is heated to a temperature above that of the final recording substrate and below that of the melted ink in the printing apparatus; (2) the final recording substrate is heated to a temperature above that of the intermediate transfer member and below that of the melted ink in the printing apparatus; or (3) the intermediate transfer member and the final recording sheet are heated to approximately the same temperature. In one specific embodiment, the printing apparatus employs a piezoelectric printing process wherein droplets of the ink are caused to be ejected in imagewise pattern by oscillations of piezoelectric vibrating elements. Inks as disclosed herein can also be employed in other hot melt printing processes, such as hot melt acoustic ink jet printing, hot melt continuous stream or deflection ink jet printing, and the like. Phase change inks as disclosed herein can also be used in printing processes other than hot melt ink jet printing processes.

Any suitable substrate or recording sheet can be employed, including plain papers such as XEROX 4200 papers, XEROX Image Series papers, Courtland 4024 DP paper, ruled notebook paper, bond paper, silica coated papers such as Sharp Company silica coated paper, JuJo paper, HAMMERMILL LASERPRINT paper, and the like, glossy coated papers such as XEROX Digital Color Gloss, Sappi Warren Papers LUSTROGLOSS, specialty papers such as Xerox DURAPAPER, and the like, transparency materials, fabrics, textile products, plastics, polymeric films, inorganic recording mediums such as metals and wood, and the like, transparency materials, fabrics, textile products, plastics, polymeric films, inorganic substrates such as metals and wood, and the like.

According to some embodiments, there is provided a method of jet printing an image, comprising: jetting a curable solid ink onto a print substrate to form an image; and exposing the image to radiation to cure the curable solid ink on to the print substrate, wherein the curable solid ink comprises a curable wax, an optional non-curable component, one or more monomers, an optional colorant, an amide gellant, wherein the gellant is an ester-terminated polyamide resin end-capped with isosorbide, and a photoinitiator.

Properties of the Gellants and Inks

The amide gellants containing isosorbide provide a low-cost bio-renewable content substitute to conventional gellants, such as those end-capped with alcohols. Further, the amide gellants containing isosorbide of the present embodiments are non-aromatic end-cap gellants with comparable phase-change properties to those with aromatic end-caps Prepared solid inks of the present embodiments have low jetting temperatures than previously achieved, for example, jetting temperatures of from about 100 to about 70° C., or from about 100 to about 80° C., from about 90 to about 70° C. In particular, the present embodiments also provide faster phase change characteristics, excellent curing performance, increased hardness after curing, and low shrinkage characteristics.

The present embodiments provide low energy ultraviolet (UV) curable pigmented solid inks with high reactivity and minimum shrinkage. These inks of the present embodiments contain a bio-renewable content gellant additive and were formulated with viscosities in the range of less than 20 cPs at 90° C., or from about 20 to about 5 cPS at 90° C., or from about 15 to about 8 cPs at 90° C., and a shrinkage value of less than 3%, or from about 1 to about 3%. As used herein, the shrinkage value indicates the shrinkage of the ink upon cooling from a liquid state. Significant improvements in curing rate and benchmarked hardness after curing was also shown for these inks as well as improved compatibility between components upon solidification. Extensive studies demonstrated that the concentration of non-curable resins should be less than 5 percent, or from about 1 to about 3 percent, or less than 1 percent by weight. Curing rates were obtained by plotting the hardness versus duration of exposure to UV light in s/ft (Fusions UV doped mercury D-bulb, 600 W/cm) and applying the following expressions:

$$y = m_1 + m_2 \cdot (1 - \exp(-m_3 \cdot x))$$

$$\text{Initial Hardness} = m_1$$

$$\text{Initial Slope} = m_2 \cdot m_3$$

$$\text{Final Hardness} = m_1 + m_2$$

where the initial slope is taken as the initial curing rate. The inks of the present embodiments display curing rates from about 130 to about 250 ft/s, such as from about 180 to about 250 ft/s or from about 200 to about 250 ft/s. Depending on the type of bulb used in the UV curable lamp, the characteristic output used for curing may be from about 200 nm to about 450 nm.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The examples set forth herein below and are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example 1

Isosorbide Capped Gellant Preparation

In a 1 L round-bottomed flask with overhead stirred and PTFE blade was added organoamide PPAGel-int-5 (66.11 g, 51.4 mmol) followed by 500 mL dichloromethane solvent. The mixture was stirred for 2 hours until all the organoamide was dissolved. Next, DMAP (dimethylaminopyridine, Aldrich) (0.942 g, 7.71 mmol) was added to the reaction flask, followed by DCC(N,N-dicyclohexylcarbodiimide, Aldrich) (22.28 g, 108 mmol). The mixture was stirred for 15 minutes, and went from clear to cloudy. Finally, isosorbide (Iowa Corn Board) (15.41 g, 105 mmol) was added, and the reaction was stirred overnight at ambient temperature. The next day, the DCHU byproduct was removed by filtration, and the dichloromethane solvent was removed in vacuo to furnish a foamy solid gel. The product was re-dissolved in 500 mL dichloromethane, and allowed to stand in a refrigerator for 48 h to precipitate any residual DCHU and DMAP residues. After 48 hours, the chilled dichloromethane solution was filtered, and the solvent was removed in vacuo to give 77 g of isosorbide-capped gellants as an amber-coloured gel. Following the above steps, the following compounds were produced:

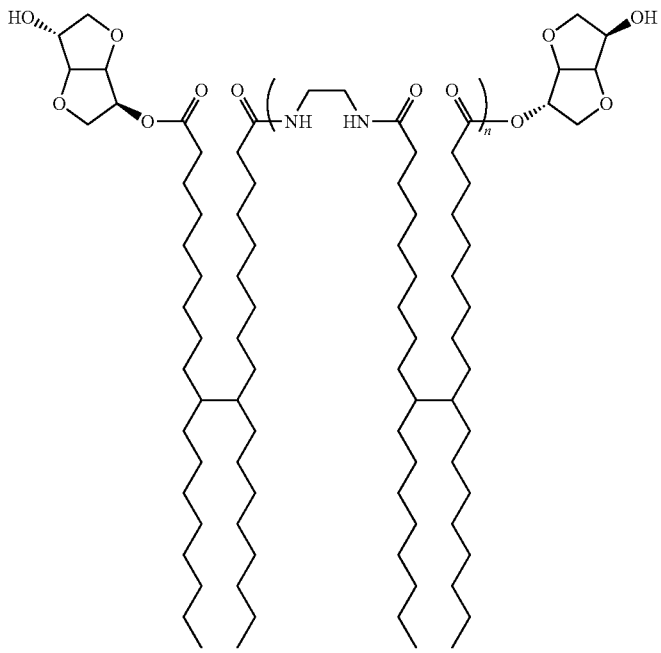

where n is ~0 to 4.

Figure 4:
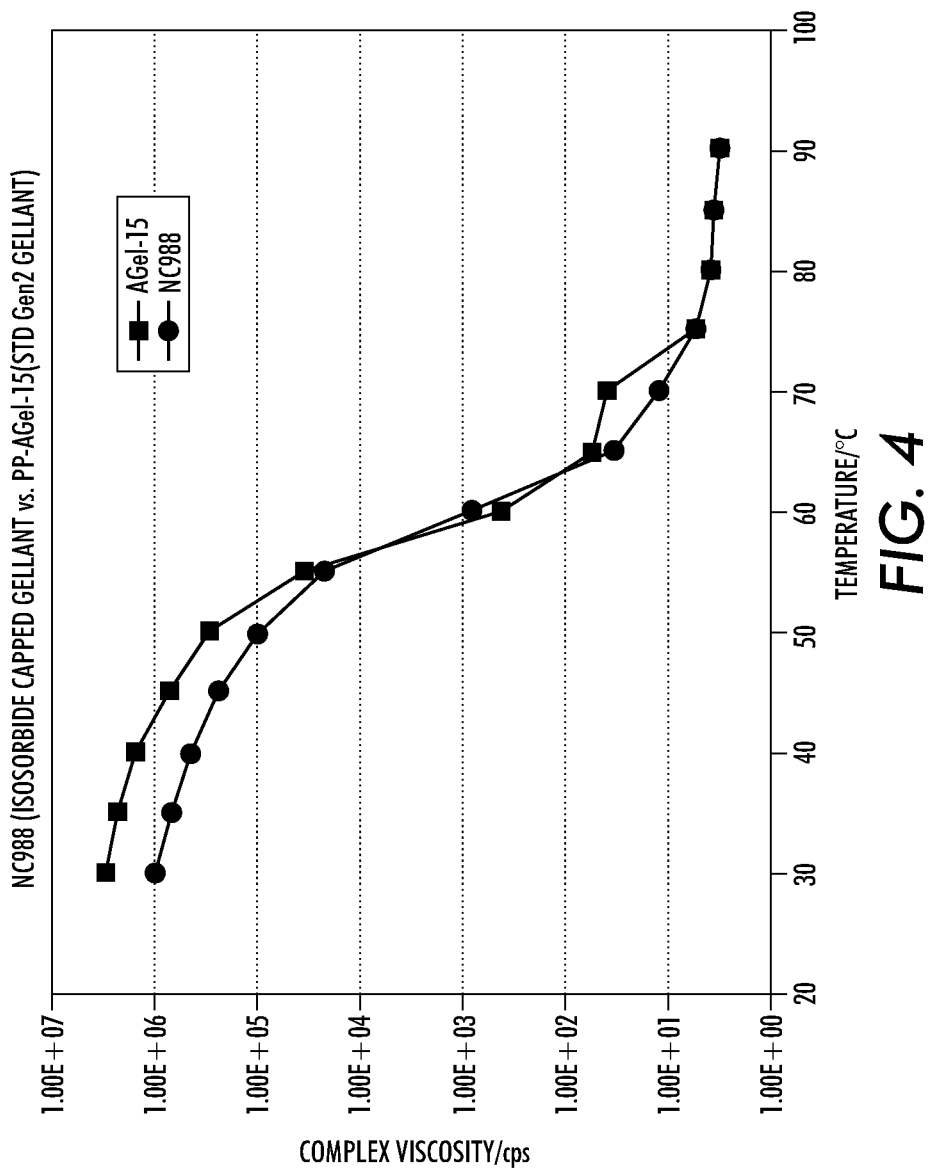
FIG. 4. Rheology (complex viscosity) comparison of a mixture containing isosorbide-capped amide gellant, wax and SR9003 monomer vs. a mixture containing standard amide gellant, wax and SR9003 monomer as a function of temperature.

FIG. 4 shows the results of test demonstrating the suitability of a formulation containing isosorbide gellant, wax and SR9003 monomer as a phase-change material. The viscosity profile of the formulation containing isosorbide gellant is comparable to a benchmark gellant, PP-AGel-15.

Example 1a

Standard Gellant Preparation (PP-Agel-int-15)

To a 5-gallon stainless steel reactor equipped with an overhead mixer was added a solution containing 7.5 kg of 42.4% AGel-int-8 solution in toluene (3.18 kg organoamide, acid#=87.5, 2.48 mol) followed by 3.82 kg toluene. Next, 66 g DMAP (dimethylaminopyridine, 0.54 mol) was added, and the reactor was purged with $N_2$. Next, a mixture of 1.05 kg DCC (dicyclohexylcarbodiimide, Aldrich corporation, 5.09 mol, 2.05 eq.) and 0.47 kg toluene was pumped into the reactor at a feed rate of approx. 50 g/min. After the DCC/toluene addition was completed, the slurry was mixed for 15 minutes time. Finally, 684 g of phenyl glycol (Aldrich, 4.95 mol, 2 eq.) were added and the mixture was allowed to mix for 4 hours time. The reactor was heated to 45° C., 1 kg of toluene was added, and the reaction mixture was filtered through a bag filter while still warm. After filtration, the filtercake containing DCHU byproduct was discarded, and the filtrate was charged back into the reactor and allowed to stand overnight at room temperature. The following day, the filtrate was vacuum distilled at 105° C. to remove the toluene solvent, and the molten gellant product concentrate was discharged into steel pails to cool and solidify. Acid# of standard gellant product: 0.68.

Example 2

Ink Preparation

The isosorbide-capped amide gellant was formulated into a UV curable gel ink according to the following procedure using the relative proportions described in the table below (Example 2A). To a 150 mL beaker heated to 90° C. was added SR833S monomer (tricyclodecanediol diacrylate from Sartomer Chemical Corp.), SR399LV (dipentaerythritol pentaacrylate, from Sartomer Chemical Co.), Irgacure 379, 819, and 127 (photoinitiators, from BASF Corp.), and Irgastab UV10 (in-can stabilizer, from BASF corp.). The mixture was heated with stirring until the solid components were dissolved. Next, isosorbide-capped amide gellant and Unilin 350 acrylate were added and the mixture was stirred with heating for approximately 1 hour until the contents were completely dissolved. The base was filtered, then a Cyan pigment dispersion concentrate in SR9003 was added, and the mixture was stirred for 1 hour more, followed by a second filtration.

In a similar fashion, a control ink was prepared using a current standard amide gellant (phenyl glycol-capped amide gellant) (Example 2B)

Example 2A

Isosorbide-Capped Gellant Ink

| Component | Wt % |
| --- | --- |
| Isosorbide-capped amide gellant | 7.5% |
| Unilin-350 acrylate | 5% |
| SR833S (tricyclodecanediol diacrylate) | 54.8% |
| SR399LV (dipentaerthritol pentaacrylate) | 5% |
| Irgacure 379 | 3% |
| Irgarcure 819 | 1% |
| Irgacure 127 | 3.5% |
| Irgastab UV10 | 0.2% |
| 15 wt % cyan pigment dispersion/SR9003 | 20% |
| TOTAL | 100% |

Example 2B

Control Ink

| Component | Wt % |
| --- | --- |
| Phenyl glycol-capped amide gellant | 7.5% |
| Unilin-350 acrylate | 5% |
| SR9003 (PONPGDA) | 54.8% |
| SR399LV (dipentaerthritol pentaacrylate) | 5% |
| Irgacure 379 | 3% |
| Irgarcure 819 | 1% |
| Irgacure 127 | 3.5% |
| Irgastab UV10 | 0.2% |
| 15 wt % cyan pigment dispersion/SR9003 | 20% |
| TOTAL | 100% |

Rheological data was collected on the 2 inks using an RFS-III controlled strain instrument from TA Instruments using a 50 mm parallel plate geometry with a dynamic temperature step test. The viscosity profile was comparable to benchmark UV curable gel ink.

Figure 5:
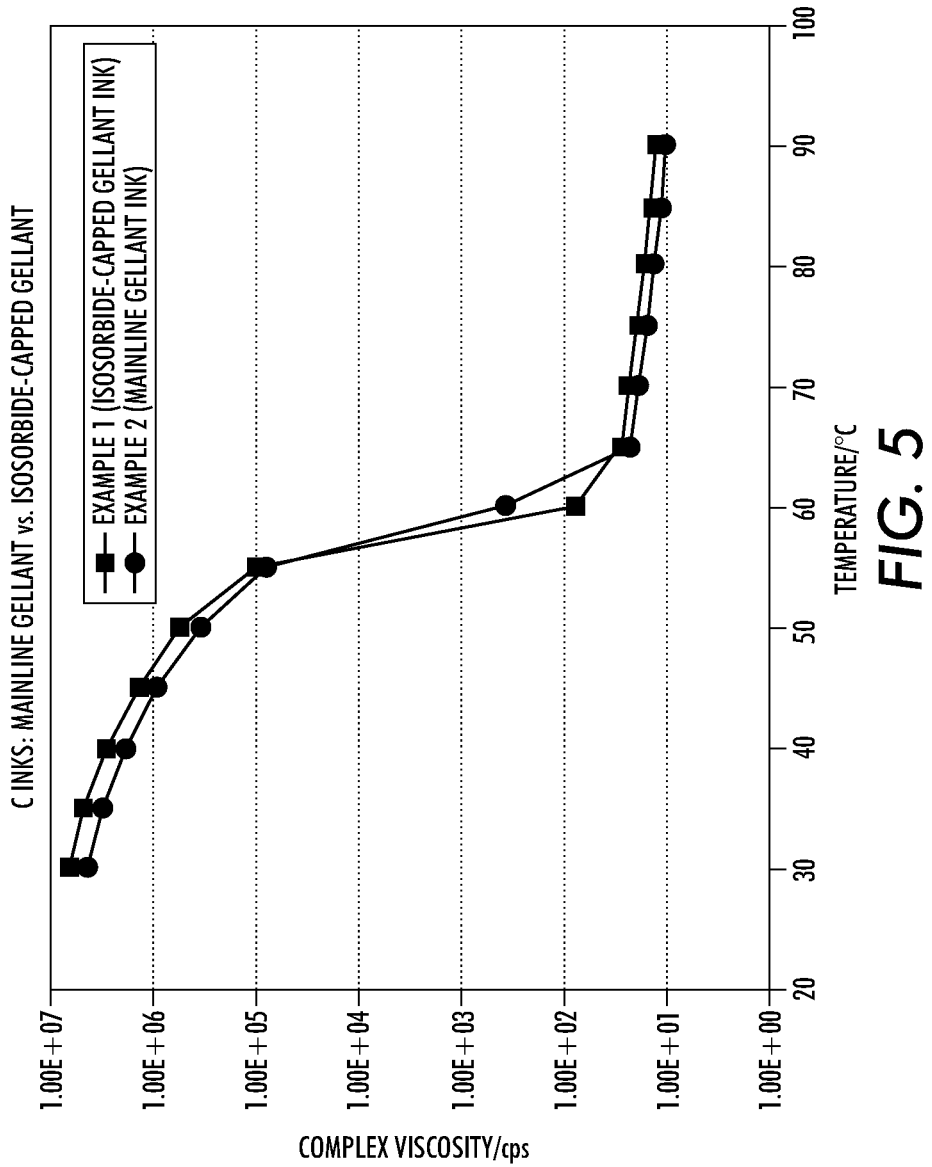
FIG. 5. Rheology comparison of isosorbide-capped amide gellant ink vs. standard gellant ink.
Figure 6:
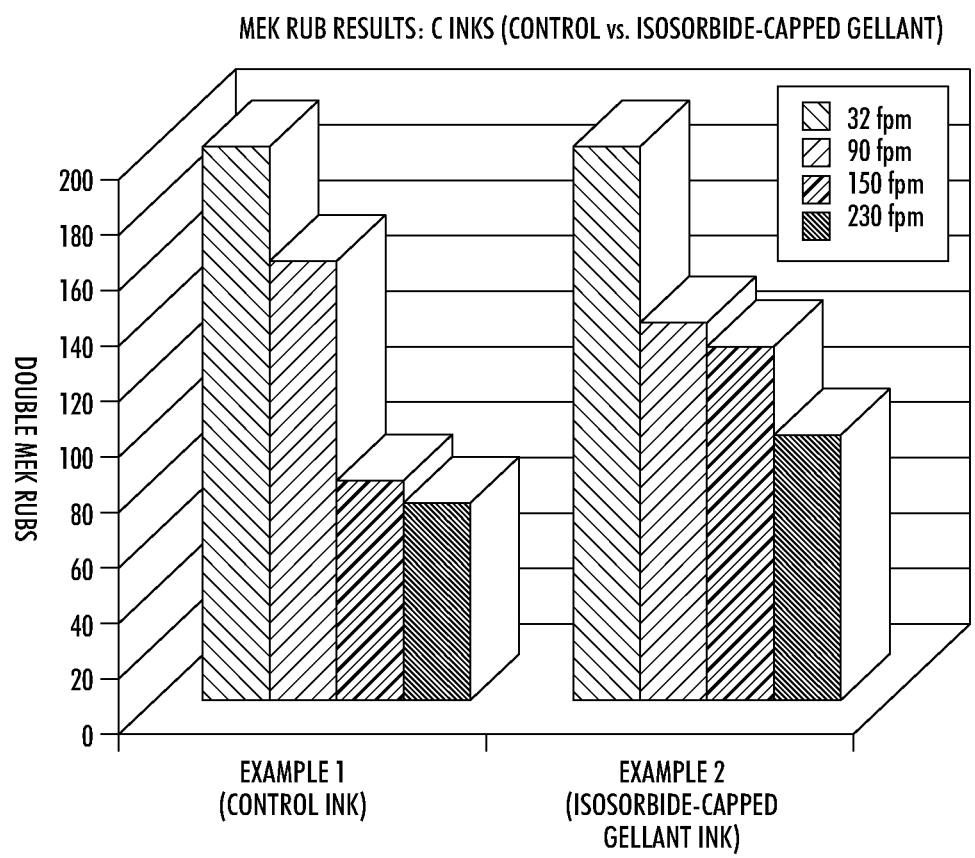
FIG. 6. MEK rub comparison tests between control ink (containing standard gellant) and Isosorbide-capped gellant inks.

Cure Testing of Ink: Ink compositions prepared in Examples 2A and 2B were printed on uncoated Mylar sheets using a K-printing proofer and cured with a 600 W Fusions UV Lighthammer UV curing lamp fitted with a mercury D-bulb under a moving conveyor belt moving with belt speeds of 32, 90, 150, and 230 fpm. The cured films were subjected to MEK double rubs with a cotton swab to evaluate cure. The MEK double rub test involves rubbing a cotton swab dipped in MEK solvent across the print back and forth until the printed ink rubs off (ASTM D4752 Solvent Resistance Rub Test). The greater the number of MEK double rubs before ink removal, the greater the degree of cure. The bar chart below summarizes the film MEK rub resistance properties of the experimental ink (Example 2A) vs. our standard ink (Example 2B). The results in FIG. 5 below show a comparable cure response between the 2 inks. FIG. 6 shows the results of MEK rub comparison tests between Control and Isosorbide-capped gellant inks.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. Unless specifically recited in a claim, steps or components of claims should not be implied or imported from the specification or any other claims as to any particular order, number, position, size, shape, angle, color, or material.

All the patents and applications referred to herein are hereby specifically, and totally incorporated herein by reference in their entirety in the instant specification.

What is claimed is:

1. An amide gellant compound of the formula:

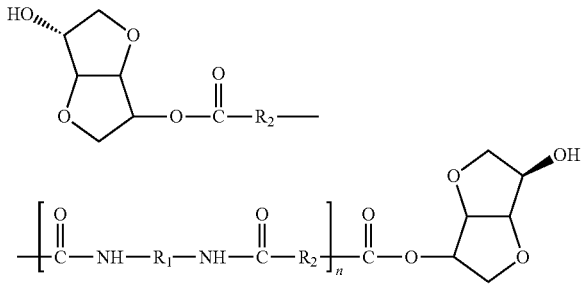

wherein n is 1 to 10, and
wherein $R_1$ is selected from the group consisting of:
 (i) a substituted or unsubstituted alkylene group having from about 1 carbon atom to about 12 carbon atoms,
 (ii) a substituted or unsubstituted arylene group having from about 1 carbon atom to about 15 carbon atoms,
 (iii) a substituted or unsubstituted arylalkylene group having from about 6 carbon atoms to about 32 carbon atoms, and
 (iv) a substituted or unsubstituted alkylarylene group having from about 5 carbon atoms to about 32 carbon atoms;
wherein $R_2$ is selected from the group consisting of:
 (i) a substituted or unsubstituted alkylene groups having from about 1 carbon atom to about 54 carbon atoms
 (ii) substituted or unsubstituted arylene groups having from about 5 carbon atoms to about 15 carbon atoms,
 (iii) substituted or unsubstituted arylalkylene groups having from about 6 carbon atoms to about 32 carbon atoms, and
 (iv) substituted or unsubstituted alkylarylene groups having from about 6 carbon atoms to about 32 carbon atoms.

2. The amide gellant compound of claim 1, wherein the alkylene group of $R_1$ or $R_2$ is a divalent aliphatic group or alkyl group, including linear and branched, saturated and unsaturated, and cyclic and acyclic, and wherein the alkylene group optionally comprises heteroatoms selected from the group consisting of oxygen, nitrogen, sulfur, silicon, phosphorus, and boron.

3. An amide gellant compound the formula:

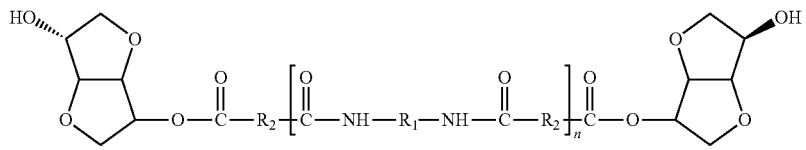

wherein n is 1 to 10; and
R₁ is a substituted or unsubstituted arylene group having from about 5 carbon atom to about 8 carbon atoms, and R₇ is a substituted or unsubstituted arylene group having from about 5 carbon atom to about 15 carbon atoms, wherein the arylene group of R₁ or R₂ is a divalent aromatic group or aryl group.

4. An amide gellant compound the formula:

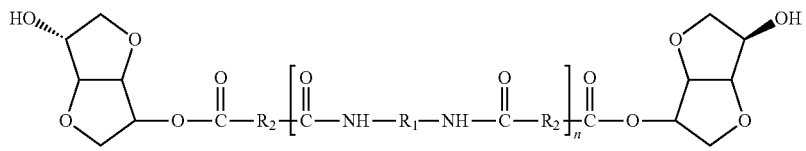

wherein n is 0 to 10; and
R₁ or R₂ is a substituted or unsubstituted arylalkylene group having from about 6 carbon atom to about 32 carbon atoms, wherein the arylalkylene group of R₁ or R₂ is a divalent arylalkyl group, wherein the alkyl portion of the arylalkylene group is linear or branched, saturated or unsaturated, and cyclic or acyclic, and wherein the alkylene group, in either the aryl or the alkyl portion of the arylalkylene group, optionally comprises heteroatoms selected from the group consisting of oxygen, nitrogen, sulfur, silicon, phosphorus, and boron.

5. An amide gellant compound the formula:

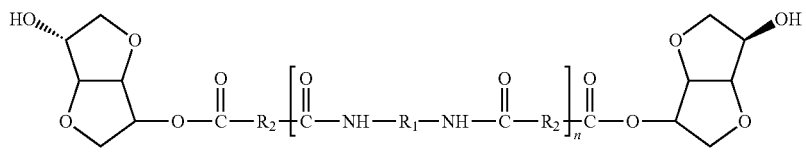

wherein n is 0 to 10; and
R₁ is a substituted or unsubstituted alkylarylene group having from about 6 carbon atom to about 32 carbon atoms, and R₂ is a substituted or unsubstituted alkylarylene group having from about 6 carbon atom to about 32 carbon atoms, wherein the alkylarylene group of R₁ or R₂ is a divalent alkylaryl group, wherein the alkyl portion of the alkylarylene group is linear or branched, saturated or unsaturated, and cyclic or acyclic, and wherein the alkylarylene group, in either the aryl or the alkyl portion of the alkylarylene group, optionally comprises het-eroatoms selected from the group consisting of oxygen, nitrogen, sulfur, silicon, phosphorus, and boron.

6. The amide gellant compound of claim 1, wherein the substituents on substituted alkylene, arylene, arylalkylene, and alkylarylene groups of R₁ or R₂ is selected from the group consisting of halogen atoms, cyano groups, pyridine groups, pyridinium groups, ether groups, aldehyde groups, ketone groups, ester groups, amide groups, carbonyl groups, thiocarbonyl groups, phosphine groups, phosphonium groups, phosphate groups, nitrile groups, mercaptosulfide groups, nitro groups, nitroso groups, acyl groups, acid anhydride groups, azide groups, azo groups, cyanato groups, urethane groups, and urea groups.

7. An amide gellant compound the formula:

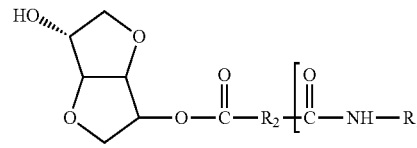

wherein n is 1 to 10, and
wherein R₁ is selected from the group consisting of:
(i) a substituted or unsubstituted alkylene group having from about 1 carbon atom to about 12 carbon atoms,
(ii) a substituted or unsubstituted arylene group having from about 1 carbon atom to about 15 carbon atoms, (iii) a substituted or unsubstituted arylalkylene group having from about 6 carbon atoms to about 32 carbon atoms, and
(iv) a substituted or unsubstituted alkylarylene group having from about 5 carbon atoms to about 32 carbon atoms;
wherein $R_2$ is:
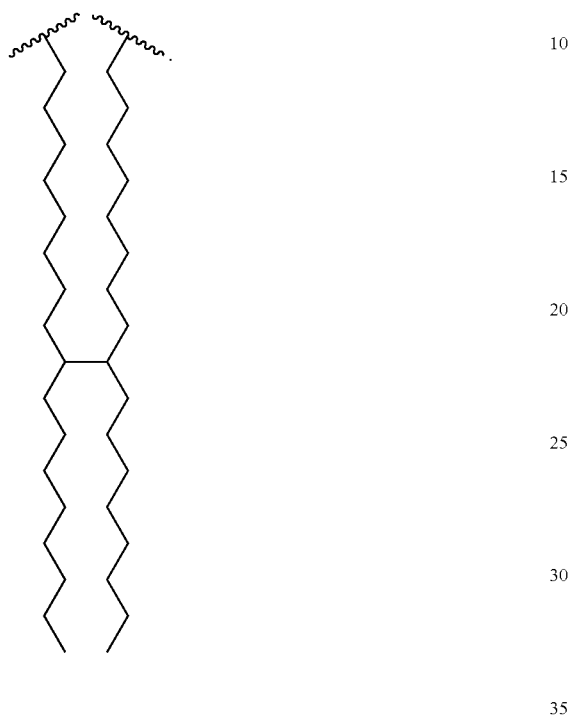
8. An amide gellant compound of the formula:
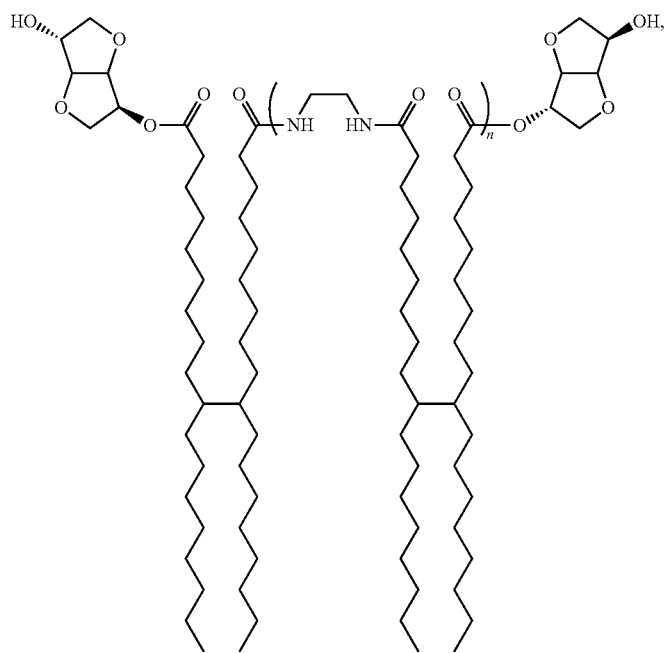
where n is 0 to 10.

9. The amide gellant compound of claim 1, wherein $R_1$ is a substituted or unsubstituted alkylene group having from about 1 carbon atom to about 5 carbon atoms.

10. An amide gellant compound of the formula:

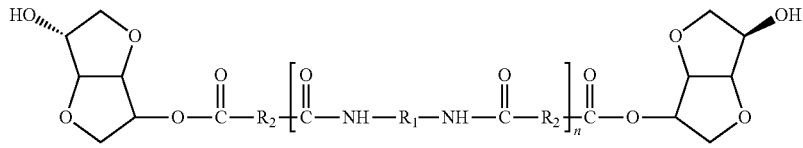

wherein n is 1 to 10,
$R_1$ is a substituted or unsubstituted alkylene group having from about 1 carbon atom to about 12 carbon atoms; and
$R_2$ is a substituted or unsubstituted alkylene groups having from about 1 carbon atom to about 54 carbon atoms.

11. The amide gellant compound of claim 10, wherein $R_1$ is a substituted or unsubstituted alkylene group having from about 1 carbon atom to about 5 carbon atoms.

12. The amide gellant compound of claim 10, wherein $R_2$ is a substituted or unsubstituted alkylene group having from about 1 carbon atom to about 36 carbon atoms.

\* \* \* \* \*